(12) United States Patent
McKenzie et al.

(10) Patent No.: US 7,273,744 B2
(45) Date of Patent: Sep. 25, 2007

(54) HEPARANASE-LIKE POLYPEPTIDES

(75) Inventors: Edward Alexander McKenzie, Abingdon (GB); Alasdair Craig Stamps, Abingdon (GB); Jonathan Alexander Terrett, Abingdon (GB); Kerry Louise Tyson, Abingdon (GB)

(73) Assignee: UCB Pharma S.A., Brussels (BE)

( * ) Notice: Subject to any disclaimer, the term of this patent is extended or adjusted under 35 U.S.C. 154(b) by 786 days.

(21) Appl. No.: 10/177,245

(22) Filed: Jun. 21, 2002

(65) Prior Publication Data

US 2003/0083254 A1 May 1, 2003

Related U.S. Application Data

(63) Continuation of application No. PCT/GB00/04963, filed on Dec. 21, 2000.

(30) Foreign Application Priority Data

Dec. 22, 1999 (GB) ................................. 9930392.7
Apr. 7, 2000 (GB) ................................. 0008713.0

(51) Int. Cl.
 *C12N 9/00* (2006.01)
 *C12N 9/88* (2006.01)
(52) U.S. Cl. ............................. 435/232; 435/4; 435/6; 435/69.1; 435/183; 435/195; 435/200; 424/94.1; 536/23.2
(58) Field of Classification Search .................... 435/4, 435/6, 69.1, 183, 200; 424/94.1; 530/350
See application file for complete search history.

(56) References Cited

U.S. PATENT DOCUMENTS

| | | | |
|---|---|---|---|
| 4,882,318 A | 11/1989 | Vlodavsky et al. | |
| 5,567,417 A | 10/1996 | Sasisekharan et al. | |
| 5,968,822 A | 10/1999 | Pecker et al. | |
| 7,101,706 B1 * | 9/2006 | Pecker et al. | ............... 435/325 |

FOREIGN PATENT DOCUMENTS

| | | |
|---|---|---|
| WO | WO97/11684 | 4/1997 |
| WO | WO99/11798 | 3/1999 |
| WO | WO99/21975 | 5/1999 |
| WO | WO99/40207 | 8/1999 |
| WO | WO 99/43830 | 9/1999 |
| WO | WO99/43830 | 9/1999 |
| WO | WO 01/79253 A1 * | 10/2001 |

OTHER PUBLICATIONS

Bame et al., Biochem J., 336:191-200 (1998).
Becker et al., J Natl Cancer Inst., 77:417-424 (1986).
Database EMBL 'Online! European Molecular Biology Laboratories; Acc. No. AF184967, Nov. 2, 1999, Podyma et al., "Rattus norvegicus heparanase (Hep)mRNA, comlete cds."
Database EMBL 'Online! European Molecular Biology Laboratories; Acc. No. AI222323; EST, Oct. 28, 1998, NCI-CGAP: "qg97h02.x1 Soares__NFL__T__GBCS1 Homo sapiens cDNA clone IMAGE:1843155 3', mRNA sequence".
Database EMBL 'Online! European Molecular Biology Laboratories; Acc. No. AI019269; EST, Jun. 18, 1998, Marra et al.: "ub22a07.r1 Soares 2NBMT Mus musculus cDNA clone IMAGE1378452 5', mRNA sequence".
Fairbanks et al., J Biol Chem, 274:29587-29590 (1999).
Freeman et al., Biochemical Journal, 342:361-368 (1999).
Godder et al., J. Cell Physiol., 148:274-280 (1991).
Haimovitz-Friedman et al., Blood, 78:789-796 (1991).
Hoogewerf et al., J Biol Chem, 270:3268-3277 (1995).
Hulett et al., Nature Med, 5:803-809 (1999).
Klein et al., BBRC, 73:569-576 (1976).
Kosir et al., J Surg Res, 67:98-105 (1997).
Kosir et al., Journal of Surgical Research, 81:42-47 (1999).
Kussie et al., Biochem Biophys Res Common, 261:183-187 (1999).
Matzner et al., Biochem, 51:519-524 (1992).
McBubbin et al., Biochem J, 256:775-783 (1999).
McKenzie et al , Biochemical and Biophysical Research Communications, 276:1170-1177 (2000).
Nakajima et al., Science, 220:611-613 (1983).
Nakajima et al., Cancer Letters, 31:277-283 (1986).
Ogren et al., J Biol Chem, 250:2690-2697 (1975).
Parish et al., Int J Cancer, 40:511-518 (1987).
Rapraeger et al., Science, 252:1705-1708 (1991).
Savion et al., J Cell Physiol, 130:77-84 (1987).
Sewell et al., Biochem J, 264:777-783 (1989).
Snow et al., Neuron, 12:219-234 (1996).
Vettel et al., Eur J Immunol, 21:2247-2251 (1991).
Vlodavsky et al., Cancer Res, 43:2704-2711 (1983).
Vlodavsky et al., Invasion Metastasis, 12:112-127 (1992).
Vlodavsky et al., Nature Med, 5:793-802 (1999).
Whitelock et al., J Biol Chem, 271:10079-10086 (1996).
Yahalom et al., Leukemia Res, 12:711-717 (1988).

* cited by examiner

*Primary Examiner*—Manjunath Rao

(57) ABSTRACT

The present invention provides a homologue to heparanase which is present in three splice variants.

3 Claims, 20 Drawing Sheets

Figure 1

```
              9          18          27          36          45          54
5' ATC CAG AGC NTC TCA GGG AAG GAC GTA AAA ACG AGA CCC TTT GCT CTG TAC CCA 63         72          81          90          99         108
   GAC GGT ACA ACG GCA TGG TTT GGA TTC CTC CCT CTG CTT CCT GAC CCT AGA GGG 117        126         135         144         153         162
   TTA AAT TAG GAG GGT ACA ACG CCA CCC TTT TCT CCT CCT TCC CGC CTG CTC CCC 171        180         189         198         207         216
   TCC CCT TAC CTT TAA AAA GTT AAA AAA TGT CTG CAG TAG AAA TCT CTT AAA GGG 225        234         243         252         261         270
   GCG GTG CCG GTG TAC GAG TTC TCT TGG CAA GAG TCA CGG GGA AGG CTG GCT AGG 279        288         297         306         315         324
   GGC GTG AGT TCG CTC CAC CAG CAC CAA AAC ACT GAA AAA AAA AAT TAA AAA AAA 333        342         351         360         369         379
   TTA AAA AAA AAA AAA GAA AAA AAC AAA ACG AGC GAG CGA GCG AGC GAG AGA GAG 387        396         405         414         423         432
   AGA GAG CGG GAG AGA GAG AGA GTG TGT GTG TGT TGG GGG GGT GGT GGG AGG AAG 441        450         459         468         477         486
   GGA AAA AAA GGG GGG AAA AAG GCG GAC GAG AGT GTG TGT GTG TTG GGG GGG TGG 495        504         513         522         531         540
   TGG GAG GAA GGG AAA AAA AGG GGG GAA AAA GGC GGA CAG ACA CAC ACT TTA GAT 549        558         567         576         585         594
   AAG GAC AAT TAG TCA CTA GCG AGA CCC AGT AGG AAG AGA GGT TTA AAT CAG AGG
                                                                   Inr
             603        612         621         630         639         648
   GAT TGA ATG AGG GTG CTT TGT GCC TTC CCT GAA GCC ATG CCC TCC AGC AAC TCC
   --- --- --- --- --- --- --- --- --- --- --- --- --- --- --- --- --- ---
        *   M   R   V   L   C   A   F   P   E   A   M   P   S   S   N   S 657        666         675         684         693         702
   CGC CCC CCC GCG TGC CTA GCC CCG GGG GCT CTC TAC TTG GCT CTG TTG CTC CAT
   --- --- --- --- --- --- --- --- --- --- --- --- --- --- --- --- ---
    R   P   P   A   C   L   A   P   G   A   L   Y   L   A   L   L   L   H 711        720         729         738         747         756
   CTC TCC CTT TCC TCC CAG GCT GGA GAC AGG AGA CCC TTG CCT GTA GAC AGA GCT
   --- --- --- --- --- --- --- --- --- --- --- --- --- --- --- --- ---
    L   S   L   S   S   Q   A   G   D   R   R   P   L   P   V   D   R   A
```

```
            765         774         783         792         801         810
GCA GGT TTG AAG GAA AAG ACC CTG ATT CTA CTT GAT GTG AGC ACC AAG AAC CCA
--- --- --- --- --- --- --- --- --- --- --- --- --- --- --- --- --- ---
 A   G   L   K   E   K   T   L   I   L   L   D   V   S   T   K   N   P 819         828         837         846         855         864
GTC AGG ACA GTC AAT GAG AAC TTC CTC TCT CTG CAG CTG GAT CCG TCC ATC ATT
--- --- --- --- --- --- --- --- --- --- --- --- --- --- --- --- --- ---
 V   R   T   V   N   E   N   F   L   S   L   Q   L   D   P   S   I   I 873         882         891         900         909         918
CAT GAT GGC TGG CTC GAT TTC CTA AGC TCC AAG CGC TTG GTG ACC CTG GCC CGG
--- --- --- --- --- --- --- --- --- --- --- --- --- --- --- --- --- ---
 H   D   G   W   L   D   F   L   S   S   K   R   L   V   T   L   A   R 927         936         945         954         963         972
GGA CTT TCG CCC GCC TTT CTG CGC TTC GGG GGC AAA AGG ACC GAC TTC CTG CAG
--- --- --- --- --- --- --- --- --- --- --- --- --- --- --- --- --- ---
 G   L   S   P   A   F   L   R   F   G   G   K   R   T   D   F   L   Q 981         990         999        1008        1017        1026
TTC CAG AAC CTG AGG AAC CCG GCG AAA AGC CGC GGG GGC CCG GGC CCG GAT TAC
--- --- --- --- --- --- --- --- --- --- --- --- --- --- --- --- --- ---
 F   Q   N   L   R   N   P   A   K   S   R   G   G   P   G   P   D   Y 1035        1044        1053        1062        1071        1080
TAT CTC AAA AAC TAT GAG GAT GAC ATT GTT CGA AGT GAT GTT GCC TTA GAT AAA
--- --- --- --- --- --- --- --- --- --- --- --- --- --- --- --- --- ---
 Y   L   K   N   Y   E   D   D   I   V   R   S   D   V   A   L   D   K 1089        1098        1107        1116        1125        1134
CAG AAA GGC TGC AAG ATT GCC CAG CAC CCT GAT GTT ATG CTG GAG CTC CAA AGG
--- --- --- --- --- --- --- --- --- --- --- --- --- --- --- --- --- ---
 Q   K   G   C   K   I   A   Q   H   P   D   V   M   L   E   L   Q   R 1143        1152        1161        1170        1179        1188
GAG AAG GCA GCT CAG ATG CAT CTG GTT CTT CTA AAG GAG CAA TTC TCC AAT ACT
--- --- --- --- --- --- --- --- --- --- --- --- --- --- --- --- --- ---
 E   K   A   A   Q   M   H   L   V   L   L   K   E   Q   F   S   N   T 1197        1206        1215        1224        1233        1242
TAC AGT AAT CTC ATA TTA ACA GCC AGG TCT CTA GAC AAA CTT TAT AAC TTT GCT
--- --- --- --- --- --- --- --- --- --- --- --- --- --- --- --- --- ---
 Y   S   N   L   I   L   T   A   R   S   L   D   K   L   Y   N   F   A 1251        1260        1269        1278        1287        1296
GAT TGC TCT GGA CTC CAC CTG ATA TTT GCT CTA AAT GCA CTG CGT CGT AAT CCC
--- --- --- --- --- --- --- --- --- --- --- --- --- --- --- --- --- ---
 D   C   S   G   L   H   L   I   F   A   L   N   A   L   R   R   N   P 1305        1314        1323        1332        1341        1350
```

```
AAT AAC TCC TGG ANC AGT TCT AGT GCC CTG    AGT CTG TTG AAG TAC AGC GCN AGC
--- --- --- --- --- --- --- --- --- ---    --- --- --- --- --- --- --- ---
 N   N   S   W   X   S   S   S   A   L      S   L   L   K   Y   S   A   S 1359        1368        1377        1386        1395        1404
AAA AAG TAC AAC ATT TCT TGG GAA CTG GGT AAT GAG CCA AAT AAC TAT CGG ACC
--- --- --- --- --- --- --- --- --- --- --- --- --- --- --- --- --- ---
 K   K   Y   N   I   S   W   E   L   G   N   E   P   N   N   Y   R   T

1413
ATG CAT GGC CGG
--- --- --- ---
 M   H   G   R 1425        1434        1443        1452        1461        1470
GCA GTA AAT GGC AGC CAG TTG GGA AAG GAT TAC ATC CAG CTG AAG AGC CTG TTG
--- --- --- --- --- --- --- --- --- --- --- --- --- --- --- --- --- ---
 A   V   N   G   S   Q   L   G   K   D   Y   I   Q   L   K   S   L   L 1479        1488        1497        1506        1515        1524
CAG CCC ATC CGG ATT TAT TCC AGA GCC AGC TTA TAT GGC CCT AAT ATT GGG CGG
--- --- --- --- --- --- --- --- --- --- --- --- --- --- --- --- --- ---
 Q   P   I   R   I   Y   S   R   A   S   L   Y   G   P   N   I   G   R 1533        1542        1551        1560        1569        1578
CCG AGG AAG AAT GTC ATC GCC CTC CTA GAT GGA TTC ATG AAG GTG GCA GGA AGT
--- --- --- --- --- --- --- --- --- --- --- --- --- --- --- --- --- ---
 P   R   K   N   V   I   A   L   L   D   G   F   M   K   V   A   G   S 1587        1596        1605        1614        1623        1632
ACA GTA GAT GCA GTT ACC TGG CAA CAT TGC TAC ATT GAT GGC CGG GTG GTC AAG
--- --- --- --- --- --- --- --- --- --- --- --- --- --- --- --- --- ---
 T   V   D   A   V   T   W   Q   H   C   Y   I   D   G   R   V   V   K 1641        1650        1659        1668        1677        1686
GTG ATG GAC TTC CTG AAA ACT CGC CTG TTA GAC ACA CTC TCT GAC CAG ATT AGG
--- --- --- --- --- --- --- --- --- --- --- --- --- --- --- --- --- ---
 V   M   D   F   L   K   T   R   L   L   D   T   L   S   D   Q   I   R 1695        1704        1713        1722        1731        1740
AAA ATT CAG AAA GTG GTT AAT ACA TAC ACT CCA GGA AAG AAG ATT TGG CTT GAA
--- --- --- --- --- --- --- --- --- --- --- --- --- --- --- --- --- ---
 K   I   Q   K   V   V   N   T   Y   T   P   G   K   K   I   W   L   E 1749        1758        1767        1776        1785        1794
GGT GTG GTG ACC ACC TCA GCT GGA GGC ACA AAC AAT CTA TCC GAT TCC TAT GCT
--- --- --- --- --- --- --- --- --- --- --- --- --- --- --- --- --- ---
 G   V   V   T   T   S   A   G   G   T   N   N   L   S   D   S   Y   A 1803        1812        1821        1830        1839        1848
GCA GGA TTC TTA TGG TTG AAC ACT TTA GGA ATG CTG GCC AAT CAG GCC ATT GAT
```

```
                    A   G   F   L   W   L   N   T   L   G   M   L   A   N   Q   G   I   D 1857        1866        1875        1884        1893        1902
GTC GTG ATA CGG CAC TCA TTT TTT GAC CAT GGA TAC AAT CAC CTC GTG GAC CAG
 V   V   I   R   H   S   F   F   D   H   G   Y   N   H   L   V   D   Q 1911        1920        1929        1938        1947        1956
AAT TTT AAC CCA TTA CCA GAC TAC TGG CTC TCT CTC CTC TAC AAG CGC CTG ATC
 N   F   N   P   L   P   D   Y   W   L   S   L   L   Y   K   R   L   I 1965        1974        1983        1992        2001        2010
GGC CCC AAA GTC TTG GCT GTG CAT GTG GCT GGG CTC CAG CGG AAG CCA CGG CCT
 G   P   K   V   L   A   V   H   V   A   G   L   Q   R   K   P   R   P 2019        2028        2037        2046        2055        2064
GGC CGA GTG ATC CGG GAC AAA CTA AGG ATT TAT GCT CAC TGC ACA AAC CAC CAC
 G   R   V   I   R   D   K   L   R   I   Y   A   H   C   T   N   H   H 2073        2082        2091        2100        2109        2118
AAC CAC AAC TAC GTT CGT GGG TCC ATT ACA CTT TTT ATC ATC AAC TTG CAT CGA
 N   H   N   Y   V   R   G   S   I   T   L   F   I   I   N   L   H   R.

2127        2136        2145        2154        2163        2172
TCA AGA AAG AAA ATC AAG CTG GCT GGG ACT CTC AGA GAC AAG CTG GTT CAC CAG
 S   R   K   K   I   K   L   A   G   T   L   R   D   K   L   V   H   Q 2181        2190        2199        2208        2217        2226
TAC CTG CTG CAG CCC TAT GGG CAG GAG GGC CTA AAG TCC AAG TCA GTG CAA CTG
 Y   L   L   Q   P   Y   G   Q   E   G   L   K   S   K   S   V   Q   L 2235        2244        2253        2262        2271        2280
AAT GGC CAG CCC TTA GTG ATG GTG GAC GAC GGG ACC CTC CCA GAA TTG AAG CCC
 N   G   Q   P   L   V   M   V   D   D   G   T   L   P   E   L   K   P 2289        2298        2307        2316        2325        2334
CGC CCC CTT CGG GCC GGC CGG ACA TTG GTC ATC CCT CCA GTC ACC ATG GGC TTT
 R   P   L   R   A   G   R   T   L   V   I   P   P   V   T   M   G   F 2343        2352        2361        2370        2379        2388
TTT GTG GTC AAG AAT GTC AAT GCT TTG GCC TGC CGC TAC CGA TAA GCT ATC CTC
```

```
        F   V   V   K   N   V   N   A   L   A   C   R   Y   R   *

2397        2406        2415        2424        2433        2442
ACA CTC ATG GCT ACC AGT GGG CCT GCT GGG CTG CTT CCA CTC CTC CAC TCC AGT 2451        2460        2469        2478        2487        2496
AGT ATC CTC TGT TTT CAG ACA TCC TAG CAA CCA GCC CCT GCT GCC CCA TCC TGC 2505        2514        2523        2532        2541        2550
TGG AAT CAA CAC AGA CTT GCT CTC CAA AGA GAC TAA ATG TCA TAG CGT GAT CTT 2559        2568        2577        2586        2595        2604
AGC CTA GGT AGG CCA CAT CCA TCC CAA AGG AAA ATG TAG ACA TCA CCT GTA CCT 2613        2622        2631
ATA TAA GGA TAA AGG CAT GTG TAT AGA GCA AA 3'
```

Figure 2

```
            9         18        27        36        45        54
5' ATC CAG AGC NTC TCA GGG AAG GAC GTA AAA ACG AGA CCC TTT GCT CTG TAC CCA 63        72        81        90        99       108
   GAC GGT ACA ACG GCA TGG TTT GGA TTC CTC CCT CTG CTT CCT GAC CCT AGA GGG 117       126       135       144       153       162
   TTA AAT TAG GAG GGT ACA ACG CCA CCC TTT TCT CCT CCT TCC CGC CTG CTC CCC 171       180       189       198       207       216
   TCC CCT TAC CTT TAA AAA GTT AAA AAA TGT CTG CAG TAG AAA TCT CTT AAA GGG 225       234       243       252       261       270
   GCG GTG CCG GTG TAC GAG TTC TCT TGG CAA GAG TCA CGG GGA AGG CTG GCT AGG 279       288       297       306       315       324
   GGC GTG AGT TCG CTC CAC CAG CAC CAA AAC ACT GAA AAA AAA AAT TAA AAA AAA 333       342       351       360       369       378
   TTA AAA AAA AAA AAA GAA AAA AAC AAA ACG AGC GAG CGA GCG AGC GAG AGA GAG 387       396       405       414       423       432
   AGA GAG CGG GAG AGA GAG AGA GTG TGT GTG TGT TGG GGG GGT GGT GGG AGG AAG 441       450       459       468       477       486
   GGA AAA AAA GGG GGG AAA AAG GCG GAC GAG AGT GTG TGT GTG TTG GGG GGG TGG 495       504       513       522       531       540
   TGG GAG GAA GGG AAA AAA AGG GGG GAA AAA GGC GGA CAG ACA CAC ACT TTA GAT 549       558       567       576       585       594
   AAG GAC AAT TAG TCA CTA GCG AGA CCC AGT AGG AAG AGA GGT TTA AAT CAG AGG
                                                             Inr
           603       612       621       630       639       648
   GAT TGA ATG AGG GTG CTT TGT GCC TTC CCT GAA GCC ATG CCC TCC AGC AAC TCC
   --- --- --- --- --- --- --- --- --- --- --- --- --- --- --- --- --- ---
    *   M   R   V   L   C   A   F   P   E   A   M   P   S   S   N   S 657       666       675       684       693       702
   CGC CCC CCC GCG TGC CTA GCC CCG GGG GCT CTC TAC TTG GCT CTG TTG CTC CAT
   --- --- --- --- --- --- --- --- --- --- --- --- --- --- --- --- --- ---
    R   P   P   A   C   L   A   P   G   A   L   Y   L   A   L   L   L   H 711       720       729       738       747       756
   CTC TCC CTT TCC TCC CAG GCT GGA GAC AGG AGA CCC TTG CCT GTA GAC AGA GCT
   --- --- --- --- --- --- --- --- --- --- --- --- --- --- --- --- --- ---
    L   S   L   S   S   Q   A   G   D   R   R   P   L   P   V   D   R   A
```

```
           765         774         783         792         801         810
GCA GGT TTG AAG GAA AAG ACC CTG ATT CTA CTT GAT GTG AGC ACC AAG AAC CCA
--- --- --- --- --- --- --- --- --- --- --- --- --- --- --- --- --- ---
 A   G   L   K   E   K   T   L   I   L   L   D   V   S   T   K   N   P 819         828         837         844         855         864
GTC AGG ACA GTC AAT GAG AAC TTC CTC TCT CTG CAG CTG GAT CCG TCC ATC ATT
--- --- --- --- --- --- --- --- --- --- --- --- --- --- --- --- --- ---
 V   R   T   V   N   E   N   F   L   S   L   Q   L   D   P   S   I   I 873         882         891         900         909         918
CAT GAT GGC TGG CTC GAT TTC CTA AGC TCC AAG CGC TTG GTG ACC CTG GCC CGG
--- --- --- --- --- --- --- --- --- --- --- --- --- --- --- --- --- ---
 H   D   G   W   L   D   F   L   S   S   K   R   L   V   T   L   A   R 927         936         945         954         963         972
GGA CTT TCG CCC GCC TTT CTG CGC TTC GGG GGC AAA AGG ACC GAC TTC CTG CAG
--- --- --- --- --- --- --- --- --- --- --- --- --- --- --- --- --- ---
 G   L   S   P   A   F   L   R   F   G   G   K   R   T   D   F   L   Q 981         990         999        1008        1017        1026
TTC CAG AAC CTG AGG AAC CCG GCG AAA AGC CGC GGG GGC CCG GCC CCG GAT TAC
--- --- --- --- --- --- --- --- --- --- --- --- --- --- --- --- --- ---
 F   Q   N   L   R   N   P   A   K   S   R   G   G   P   G   P   D   Y 1035        1044        1053        1062        1071        1080
TAT CTC AAA AAC TAT GAG GAT GAC ATT GTT CGA AGT GAT GTT GCC TTA GAT AAA
--- --- --- --- --- --- --- --- --- --- --- --- --- --- --- --- --- ---
 Y   L   K   N   Y   E   D   I   V   R   S   D   V   A   L   D   K

1089        1098        1107        1116        1125        1134
CAG AAA GGC TGC AAG ATT GCC CAG CAC CCT GAT GTT ATG CTG GAG CTC CAA AGG
--- --- --- --- --- --- --- --- --- --- --- --- --- --- --- --- --- ---
 Q   K   G   C   K   I   A   Q   H   P   D   V   M   L   E   L   Q   R

1143        1152        1161        1170        1179        1188
GAG AAG GCA GCT CAG ATG CAT CTG GTT CTT CTA AAG GAG CAA TTC TCC AAT ACT
--- --- --- --- --- --- --- --- --- --- --- --- --- --- --- --- --- ---
 E   K   A   A   Q   M   H   L   V   L   L   K   E   Q   F   S   N   T

1197        1206        1215        1224        1233        1242
TAC AGT AAT CTC ATA TTA ACA GAG CCA AAT AAC TAT CGG ACC ATG CAT GGC CGG
--- --- --- --- --- --- --- --- --- --- --- --- --- --- --- --- --- ---
 Y   S   N   L   I   L   T   E   P   N   N   Y   R   T   M   H   G   R 1251        1260        1269        1278        1287        1296
GCA GTA AAT GGC AGC CAG TTG GGA AAG GAT TAC ATC CAG CTG AAG AGC CTG TTG
--- --- --- --- --- --- --- --- --- --- --- --- --- --- --- --- --- ---
 A   V   N   G   S   Q   L   G   K   D   Y   I   Q   L   K   S   L   L 1305        1314        1323        1332        1341        1350
```

```
CAG CCC ATC CGG ATT TAT TCC AGA GCC AGC   TTA TAT GGC CCT AAT ATT GGG CGG
--- --- --- --- --- --- --- --- ---   --- --- --- --- --- --- --- ---
 Q   P   I   R   I   Y   S   R   A   S   L   Y   G   P   N   I   G   R 1359        1368        1377        1386        1395        1404
CCG AGG AAG AAT GTC ATC GCC CTC CTA GAT GGA TTC ATG AAG GTG GCA GGA AGT
--- --- --- --- --- --- --- --- --- --- --- --- --- --- --- --- --- ---
 P   R   K   N   V   I   A   L   L   D   G   F   M   K   V   A   G   S 1413        1422        1431        1440        1449        1458
ACA GTA GAT GCA GTT ACC TGG CAA CAT TGC TAC ATT GAT GGC CGG GTG GTC AAG
--- --- --- --- --- --- --- --- --- --- --- --- --- --- --- --- --- ---
 T   V   D   A   V   T   W   Q   H   C   Y   I   D   G   R   V   V   K 1467        1476        1485        1494        1503        1512
GTG ATG GAC TTC CTG AAA ACT CGC CTG TTA GAC ACA CTC TCT GAC CAG ATT AGG
--- --- --- --- --- --- --- --- --- --- --- --- --- --- --- --- --- ---
 V   M   D   F   L   K   T   R   L   L   D   T   L   S   D   Q   I   R 1521        1530        1539        1548        1557        1566
AAA ATT CAG AAA GTG GTT AAT ACA TAC ACT CCA GGA AAG AAG ATT TGG CTT GAA
--- --- --- --- --- --- --- --- --- --- --- --- --- --- --- --- --- ---
 K   I   Q   K   V   V   N   T   Y   T   P   G   K   K   I   W   L   E 1575        1584        1593        1602        1611        1620
GGT GTG GTG ACC ACC TCA GCT GGA GGC ACA AAC AAT CTA TCC GAT TCC TAT GCT
--- --- --- --- --- --- --- --- --- --- --- --- --- --- --- --- --- ---
 G   V   V   T   T   S   A   G   G   T   N   N   L   S   D   S   Y   A 1629        1638        1647        1656        1665        1674
GCA GGA TTC TTA TGG TTG AAC ACT TTA GGA ATG CTG GCC AAT CAG GGC ATT GAT
--- --- --- --- --- --- --- --- --- --- --- --- --- --- --- --- --- ---
 A   G   F   L   W   L   N   T   L   G   M   L   A   N   Q   G   I   D 1683        1692        1701        1710        1719        1728
GTC GTG ATA CGG CAC TCA TTT TTT GAC CAT GGA TAC AAT CAC CTC GTG GAC CAG
--- --- --- --- --- --- --- --- --- --- --- --- --- --- --- --- --- ---
 V   V   I   R   H   S   F   F   D   H   G   Y   N   H   L   V   D   Q 1737        1746        1755        1764        1773        1782
AAT TTT AAC CCA TTA CCA GAC TAC TGG CTC TCT CTC CTC TAC AAG CGC CTG ATC
--- --- --- --- --- --- --- --- --- --- --- --- --- --- --- --- --- ---
 N   F   N   P   L   P   D   Y   W   L   S   L   L   Y   K   R   L   I 1791        1800        1809        1818        1827        1836
GGC CCC AAA GTC TTC GCT GTG CAT GTG GCT GGG CTC CAG CGG AAG CCA CGG CCT
--- --- --- --- --- --- --- --- --- --- --- --- --- --- --- --- --- ---
 G   P   K   V   F   A   V   H   V   A   G   L   Q   R   K   P   R   P 1845        1854        1863        1872        1881        1890
GGC CGA GTG ATC CGG GAC AAA CTA AGG ATT TAT GCT CAC TGC ACA AAC CAC CAC
```

```
    ---  ---  ---  ---  ---  ---  ---  ---  ---  ---      ---  ---  ---  ---  ---  ---  ---  ---
     G    R    V    I    R    D    K    L    R    I        Y    A    H    C    T    N    H    H 1899           1908           1917           1926           1935           1944
    AAC  CAC  AAC  TAC  GTT  CGT  GGG  TCC  ATT  ACA  CTT  TTT  ATC  ATC  AAC  TTG  CAT  CGA
    ---  ---  ---  ---  ---  ---  ---  ---  ---  ---  ---  ---  ---  ---  ---  ---  ---  ---
     N    H    N    Y    V    R    G    S    I    T    L    F    I    I    N    L    H    R 1953           1962           1971           1980           1989           1998
    TCA  AGA  AAG  AAA  ATC  AAG  CTG  GCT  GGG  ACT  CTC  AGA  GAC  AAG  CTG  GTT  CAC  CAG
    ---  ---  ---  ---  ---  ---  ---  ---  ---  ---  ---  ---  ---  ---  ---  ---  ---  ---
     S    R    K    K    I    K    L    A    G    T    L    R    D    K    L    V    H    Q 2007           2016           2025           2034           2043           2052
    TAC  CTG  CTG  CAG  CCC  TAT  GGG  CAG  GAG  GGC  CTA  AAG  TCC  AAG  TCA  GTG  CAA  CTG
    ---  ---  ---  ---  ---  ---  ---  ---  ---  ---  ---  ---  ---  ---  ---  ---  ---  ---
     Y    L    L    Q    P    Y    G    Q    E    G    L    K    S    K    S    V    Q    L 2061           2070           2079           2088           2097           2106
    AAT  GGC  CAG  CCC  TTA  GTG  ATG  GTG  GAC  GAC  GGG  ACC  CTC  CCA  GAA  TTG  AAG  CCC
    ---  ---  ---  ---  ---  ---  ---  ---  ---  ---  ---  ---  ---  ---  ---  ---  ---  ---
     N    G    Q    P    L    V    M    V    D    D    G    T    L    P    E    L    K    P 2115           2124           2133           2142           2151           2160
    CGC  CCC  CTT  CGG  GCC  GGC  CGG  ACA  TTG  GTC  ATC  CCT  CCA  GTC  ACC  ATG  GGC  TTT
    ---  ---  ---  ---  ---  ---  ---  ---  ---  ---  ---  ---  ---  ---  ---  ---  ---  ---
     R    P    L    R    A    G    R    T    L    V    I    P    P    V    T    M    G    F 2169           2178           2187           2196           2205           2214
    TTT  GTG  GTC  AAG  AAT  GTC  AAT  GCT  TTG  GCC  TGC  CGC  TAC  CGA  TAA  GCT  ATC  CTC
    ---  ---  ---  ---  ---  ---  ---  ---  ---  ---  ---  ---  ---  ---  ---
     F    V    V    K    N    V    N    A    L    A    C    R    Y    R    *

2223           2232           2241           2250           2259           2268
    ACA  CTC  ATG  GCT  ACC  AGT  GGG  CCT  GCT  GGG  CTG  CTT  CCA  CTC  CTC  CAC  TCC  AGT 2277           2286           2295           2304           2313           2322
    AGT  ATC  CTC  TGT  TTT  CAG  ACA  TCC  TAG  CAA  CCA  GCC  CCT  GCT  GCC  CCA  TCC  TGC 2331           2340           2349           2358           2367           2376
    TGG  AAT  CAA  CAC  AGA  CTT  GCT  CTC  CAA  AGA  GAC  TAA  ATG  TCA  TAG  CGT  GAT  CTT 2385           2394           2403           2412           2421           2430
    AGC  CTA  GGT  AGG  CCA  CAT  CCA  TCC  CAA  AGG  AAA  ATG  TAG  ACA  TCA  CCT  GTA  CCT 2439           2448           2457
    ATA  TAA  GGA  TAA  AGG  CAT  GTG  TAT  AGA  GCA  AA 3'
```

Figure 3

```
              9          18         27         36         45         54
5' ATC CAG AGC NTC TCA GGG AAG GAC GTA AAA ACG AGA CCC TTT GCT CTG TAC CCA 63         72         81         90         99        108
   GAC GGT ACA ACG GCA TGG TTT GGA TTC CTC CCT CTG CTT CCT GAC CCT AGA GGG 117        126        135        144        153        162
   TTA AAT TAG GAG GGT ACA ACG CCA CCC TTT TCT CCT CCT TCC CGC CTG CTC CCC 171        180        189        198        207        216
   TCC CCT TAC CTT TAA AAA GTT AAA AAA TGT CTC CAG TAG AAA TCT CTT AAA GGG 225        234        243        252        261        270
   GCG GTG CCG GTG TAC GAG TTC TCT TGG CAA GAG TCA CGG GGA AGG CTG GCT AGG 279        288        297        306        315        324
   GGC GTG AGT TCG CTC CAC CAG CAC CAA AAC ACT GAA AAA AAA AAT TAA AAA AAA 333        342        351        360        369        378
   TTA AAA AAA AAA AAA GAA AAA AAC AAA ACG AGC CAC CGA CCG AGC GAG AGA GAG 387        396        405        414        423        432
   AGA GAG CGG GAG AGA GAG AGA GTG TGT GTG TGT TGG GGG GGT GGT GGG AGG AAG 441        450        459        468        477        486
   GGA AAA AAA GGG GGG AAA AAG GCG GAC GAG AGT GTG TGT GTG TTG GGG GGG TGG 495        504        513        522        531        540
   TGG GAC GAA GGG AAA AAA AGG GGG GAA AAA GGC GGA CAG ACA CAC ACT TTA GAT 549        558        567        576        585        594
   AAG GAC AAT TAG TCA CTA GCG AGA CCC AGT AGG AAG AGA GGT TTA AAT CAG AGG
                                                             Inr
             603        612        621        630        639        648
   GAT TGA ATG AGG GTG CTT TGT GCC TTC CCT GAA GCC ATG CCC TCC AGC AAC TCC
   --- --- --- --- --- --- --- --- --- --- --- --- --- --- --- ---
         *   M   R   V   L   C   A   F   P   E   A   M   P   S   S   N   S 657        666        675        684        693        702
   CGC CCC CCC GCG TGC CTA GCC CCG GGG GCT CTC TAC TTG GCT CTG TTG CTC CAT
   --- --- --- --- --- --- --- --- --- --- --- --- --- --- --- ---
     R   P   P   A   C   L   A   P   G   A   L   Y   L   A   L   L   H

<----Hepa4F1---
             711        720        729        738        747        756
   CTC TCC CTT TCC TCC CAG GCT GGA GAC AGG AGA CCC TTG CCT GTA GAC AGA GCT
   --- --- --- --- --- --- --- --- --- --- --- --- --- --- --- ---
     L   S   L   S   S   Q   A   G   D   R   R   P   L   P   V   D   R   A
```

```
      ---------->                              <------Hepa4F2------------->
           765           774           783           792           801           810
     GCA GGT TTG AAG GAA AAG ACC CTG ATT CTA CTT GAT GTG AGC ACC AAG AAC CCA
     --- --- --- --- --- --- --- --- --- --- --- --- --- --- --- --- --- ---
      A   G   L   K   E   K   T   L   I   L   L   D   V   S   T   K   N   P 819           828           837           846           855           864
     GTC AGG ACA GTC AAT GAG AAC TTC CTC TCT CTG CAG CTG GAT CCG TCC ATC ATT
     --- --- --- --- --- --- --- --- --- --- --- --- --- --- --- --- --- ---
      V   R   T   V   N   E   N   F   L   S   L   Q   L   D   P   S   I   I <-----Hepa4R1------------->
           873           882           891           900           909           918
     CAT GAT GGC TGG CTC GAT TTC CTA AGC TCC AAG CGC TTG GTG ACC CTG GCC CGG
     --- --- --- --- --- --- --- --- --- --- --- --- --- --- --- --- --- ---
      H   D   G   W   L   D   F   L   S   S   K   R   L   V   T   L   A   R <--
           927           936           945           954           963           972
     GGA CTT TCG CCC GCC TTT CTG CGC TTC GGG GGC AAA AGG ACC GAC TTC CTG CAG
     --- --- --- --- --- --- --- --- --- --- --- --- --- --- --- --- --- ---
      G   L   S   P   A   F   L   R   F   G   G   K   R   T   D   F   L   Q --Hepa4R2------------>
           981           990           999          1008          1017          1026
     TTC CAG AAC CTG AGG AAC CCG GCG AAA AGC CGC GGG GGC CCG GGC CCG GAT TAC
     --- --- --- --- --- --- --- --- --- --- --- --- --- --- --- --- --- ---
      F   Q   N   L   R   N   P   A   K   S   R   G   G   P   G   P   D   Y 1035          1044          1053          1062          1071          1080
     TAT CTC AAA AAC TAT GAG GAT GAG CCA AAT AAC TAT CGG ACC ATG CAT GGC CGG
     --- --- --- --- --- --- --- --- --- --- --- --- --- --- --- --- --- ---
      Y   L   K   N   Y   E   D   E   P   N   N   Y   R   T   M   H   G   R 1089          1098          1107          1116          1125          1134
     GCA GTA AAT GGC AGC CAG TTG GGA AAG GAT TAC ATC CAG CTG AAG AGC CTG TTG
     --- --- --- --- --- --- --- --- --- --- --- --- --- --- --- --- --- ---
      A   V   N   G   S   Q   L   G   K   D   Y   I   Q   L   K   S   L   L 1143          1152          1161          1170          1179          1188
     CAG CCC ATC CGG ATT TAT TCC AGA GCC AGC TTA TAT GGC CCT AAT ATT GGG CGG
     --- --- --- --- --- --- --- --- --- --- --- --- --- --- --- --- --- ---
      Q   P   I   R   I   Y   S   R   A   S   L   Y   G   P   N   I   G   R 1197          1206          1215          1224          1233          1242
     CCG AGG AAG AAT GTC ATC GCC CTC CTA GAT GGA TTC ATG AAG GTG GCA GGA AGT
     --- --- --- --- --- --- --- --- --- --- --- --- --- --- --- --- --- ---
      P   R   K   N   V   I   A   L   L   D   G   F   M   K   V   A   G   S <------Hepa2F1---------->
```

```
      1251        1260        1269        1278        1287        1296
ACA GTA GAT GCA GTT ACC TGG CAA CAT TGC TAC ATT GAT GGC CGG GTG GTC AAG
--- --- --- --- --- --- --- --- --- --- --- --- --- --- --- --- --- ---
 T   V   D   A   V   T   W   Q   H   C   Y   I   D   G   R   V   V   K 1305        1314        1323        1332        1341        1350
GTG ATG GAC TTC CTG AAA ACT CGC CTG TTA GAC ACA CTC TCT GAC CAG ATT AGG
--- --- --- --- --- --- --- --- --- --- --- --- --- --- --- --- --- ---
 V   M   D   F   L   K   T   R   L   L   D   T   L   S   D   Q   I   R 1359        1368        1377        1386        1395        1404
AAA ATT CAG AAA GTG GTT AAT ACA TAC ACT CCA GGA AAG AAG ATT TGG CTT GAA
--- --- --- --- --- --- --- --- --- --- --- --- --- --- --- --- --- ---
 K   I   Q   K   V   V   N   T   Y   T   P   G   K   K   I   W   L   E

<-----Hepa2R1------------>            <-----Hepa2R2---------
      1413        1422        1431        1440        1449        1458
GGT GTG GTG ACC ACC TCA GCT GGA GGC ACA AAC AAT CTA TCC GAT TCC TAT GCT
--- --- --- --- --- --- --- --- --- --- --- --- --- --- --- --- --- ---
 G   V   V   T   T   S   A   G   G   T   N   N   L   S   D   S   Y   A ->
      1467        1476        1485        1494        1503        1512
GCA GGA TTC TTA TGG TTG AAC ACT TTA GGA ATG CTG GCC AAT CAG GGC ATT GAT
--- --- --- --- --- --- --- --- --- --- --- --- --- --- --- --- --- ---
 A   G   F   L   W   L   N   T   L   G   M   L   A   N   Q   G   I   D 1521        1530        1539        1548        1557        1566
GTC GTG ATA CGG CAC TCA TTT TTT GAC CAT GGA TAC AAT CAC CTC GTG GAC CAG
--- --- --- --- --- --- --- --- --- --- --- --- --- --- --- --- --- ---
 V   V   I   R   H   S   F   F   D   H   G   Y   N   H   L   V   D   Q 1575        1584        1593        1602        1611        1620
AAT TTT AAC CCA TTA CCA GAC TAC TGG CTC TCT CTC CTC TAC AAG CGC CTG ATC
--- --- --- --- --- --- --- --- --- --- --- --- --- --- --- --- --- ---
 N   F   N   P   L   P   D   Y   W   L   S   L   L   Y   K   R   L   I 1629        1638        1647        1656        1665        1674
GGC CCC AAA GTC TTG GCT GTG CAT GTG GCT GGG CTC CAG CGG AAG CCA CGG CCT
--- --- --- --- --- --- --- --- --- --- --- --- --- --- --- --- --- ---
 G   P   K   V   L   A   V   H   V   A   G   L   Q   R   K   P   R   P 1683        1692        1701        1710        1719        1728
GGC CGA GTG ATC CGG GAC AAA CTA AGG ATT TAT GCT CAC TGC ACA AAC CAC CAC
--- --- --- --- --- --- --- --- --- --- --- --- --- --- --- --- --- ---
 G   R   V   I   R   D   K   L   R   I   Y   A   H   C   T   N   H   H 1737        1746        1755        1764        1773        1782
AAC CAC AAC TAC GTT CGT GGG TCC ATT ACA CTT TTT ATC ATC AAC TTG CAT CGA
--- --- --- --- --- --- --- --- --- --- --- --- --- --- --- --- --- ---
 N   H   N   Y   V   R   G   S   I   T   L   F   I   I   N   L   H   R
```

```
                  <------Hepa3F1-------------->
         1791        1800        1809        1818        1827        1836
    TCA AGA AAG AAA ATC AAG CTG GCT GGG ACT CTC AGA GAC AAG CTG GTT CAC CAG
    --- --- --- --- --- --- --- --- --- --- --- --- --- --- --- --- --- ---
     S   R   K   K   I   K   L   A   G   T   L   R   D   K   L   V   H   Q 1845        1854        1863        1872        1881        1890
    TAC CTG CTG CAG CCC TAT GGG CAG GAG GGC TAA AAG TCC AAG TCA GTG CAA CTG
    --- --- --- --- --- --- --- --- --- --- --- --- --- --- --- --- --- ---
     Y   L   L   Q   P   Y   G   Q   E   G   L   K   S   K   S   V   Q   L <------Hepa3R1-------->
         1899        1908        1917        1926        1935        1944
    AAT GGC CAG CCC TTA GTG ATG GTG GAC GAC GGG ACC CTC CCA GAA TTG AAG CCC
    --- --- --- --- --- --- --- --- --- --- --- --- --- --- --- --- --- ---
     N   G   Q   P   L   V   M   V   D   D   G   T   L   P   E   L   K   P 1953        1962        1971        1980        1989        1998
    CGC CCC CTT CGG GCC GGC CGG ACA TTG GTC ATC CCT CCA GTC ACC ATG GGC TTT
    --- --- --- --- --- --- --- --- --- --- --- --- --- --- --- --- --- ---
     R   P   L   R   A   G   R   T   L   V   I   P   P   V   T   M   G   F 2007        2016        2025        2034        2043        2052
    TTT GTG GTC AAG AAT GTC AAT GCT TTG GCC TGC CGC TAC CGA TAA GCT ATC CTC
    --- --- --- --- --- --- --- --- --- --- --- --- --- --- --- --- --- ---
     F   V   V   K   N   V   N   A   L   A   C   R   Y   R   *

2061        2070        2079        2088        2097        2106
    ACA CTC ATG GCT ACC AGT GGG CCT GCT GGG CTG CTT CCA CTC CTC CAC TCC AGT 2115        2124        2133        2142        2151        2160
    AGT ATC CTC TGT TTT CAG ACA TCC TAG CAA CCA GCC CCT GCT GCC CCA TCC TGC 2169        2178        2187        2196        2205        2214
    TGG AAT CAA CAC AGA CTT GCT CTC CAA AGA GAC TAA ATG TCA TAG CGT GAT CTT 2223        2232        2241        2250        2259        2268
    AGC CTA GGT AGG CCA CAT CCA TCC CAA AGG AAA ATG TAG ACA TCA CCT GTA CCT 2277        2286        2295
    ATA TAA GGA TAA AGG CAT GTG TAT AGA GCA AA 3'
```

Figure 4

```
                    10         20         30         40         50         60
                    |          |          |          |          |          |
heparanase    --MLLRSKPALPPP-------------LMLLLLGPLGPLSPGALPRPAQ------AQDV
novel         MRVLCAFPEAMPSSNSRPPACLAPGALYLALLLHLSLSSQAGDRRPLPVDRAAGLKEKTL
               :*      *:*..         * ***  .*.. :  . *  *.:        : :
Prim.cons.    MR2L22222A2P22NSRPPACLAPGALYL2LLL222L22222222P2P22RAAGLK2222

70         80         90        100        110        120
                    |          |          |          |          |          |
heparanase    VDLDFFTQEPLHLVSPSFLSVTIDANLATDPRFLILLGSPKLRTLARGLSPAYLRFGGTK
novel         ILLDVSTKNPVRTVNENFLSLQLDPSIIHDG-WLDFLSSKRLVTLARGLSPAFLRFGGKR
              : **. *::*:: *. .***: :*..:   *  :* :*.* :* **********:*****.:
Prim.cons.    22LD22T22P222V222FLS222D22222D2R2L22L2S22L2TLARGLSPA2LRFGG22

130        140        150        160        170        180
                    |          |          |          |          |          |
heparanase    TDFLIFDPKKESTFEERSYWQSQVNQDICKYGSIPPDVEEKLRLEWPYQEQLLLREHYQK
novel         TDFLQFQNLRN---PAKSR-----------GGPGPDYYLKN-----YEDDIVRSDVALD
              **** *:  ::       :*            *. ** *      *:::::: :   .
Prim.cons.    TDFL2F22222STF222S2WQSQVNQDICKYG222PD22K2RLEWPY222222222222

190        200        210        220        230        240
                    |          |          |          |          |          |
heparanase    KFKNSTYSRSSVDVLYTFANCSGLDLIFGLNALLRTADLQWNSSNAQLLLDYCSSKGYNI
novel         KQKGCKIAQH-PDVMLELQREK------AAQMHLVLLKEQFSNTYSNLIL---T------
              * *... ::  **:  :. .       .: *  . *:...: ::*:*   :
Prim.cons.    K2K2222222S2DV22222222GLDLIF22222L22222Q2222222L2LDYC2SKGYNI 250        260        270        280        290        300
                    |          |          |          |          |          |
heparanase    SWELGNEPNSFLKKADIFINGSQLGEDFIQLHKLLR-KSTFKNAKLYGPDVGQPRRKTAK
novel         ------EPNNYRTMHGRAVNGSQLGKDYIQLKSLLQPIRIYSRASLYGPNIGRPRKNVIA
                    ***.:  .   .  :******:*:***::**:   :..*.****::*:**:..
Prim.cons.    SWELGNEPN2222222222NGSQLG2D2IQL22LL2P222222A2LYGP22G2PR22222

310        320        330        340        350        360
                    |          |          |          |          |          |
heparanase    MLKSFLKAGGEVIDSVTWHHYYLNGRTATREDFLNPDVLDIFISSVQKVFQVVESTRPGK
novel         LLDGFMKVAGSTVDAVTWQHCYIDGRVVKVMDFLKTRLLDTLSDQIRKIQKVVNTYTPGK
              :*...*..*...:*:***:*  *::**...  ***:. :** : ...:*:. :**:: ***
Prim.cons.    2L22F2K22G222D2VTW2H2Y22GR22222DFL2222LD2222222K222VV2222PGK 370        380        390        400        410        420
                    |          |          |          |          |          |
heparanase    KVWLGETSSAYGGGAPLLSDTFAAGFMWLDKLGLSARMGIEVVMRQVFFGAGNYHLVDEN
novel         KIWLEGVVTTSAGGTNNLSDSYAAGFLWLNTLGMLANQGIDVVIRHSFFDHGYNHLVDQN
```

```
             *:**     . ::  .**:                 ***::****:**:.**: *. **:**:*: **. *  ****:*
Prim.cons.   K2WL22222222GG222LSD22AAGF2WL22LG22A22GI2VV2R22FF22G22HLVD2N 430       440       450       460       470       480
                   |         |         |         |         |         |
heparanase   FDPLPDYWLSLLFKKLVGTKVLMASVQGSKRR--------KLRVYLHCTNTDNPRYKEG
novel        FNPLPDYWLSLLYKRLIGPKVLAVHVAGLQRKPRPGRVIRDKLRIYAHCTNHHNHNYVRG
             *:**********:*:*:*.***  . * * :*:        ***:* ****  .*  .* .*
Prim.cons.   F2PLPDYWLSLL2K2L2G2KVL222V2G22R2PRPGRVIRDKLR2Y2HCTN22N22Y22G 490       500       510       520       530       540
                   |         |         |         |         |         |
heparanase   DLTLYAINLHNVTKYLRLPYPFSNKQVDKYLLRPLGPHGLLSKSVQLNGLTLKMVDDQTL
novel        SITLFIINLHRSRKKIKLAGTLRDKLVHQYLLQPYGQEGLKSKSVQLNGQPLVMVDDGTL
             .:**: ****.  * ::*. .: :* *.:***:* * .** ******** .* **** **
Prim.cons.   22TL22INLH222K222L222222K2V22YLL2P2G22GL2SKSVQLNG22L2MVDD2TL 550       560       570
                   |         |         |
heparanase   PPLMEKPLRPGSSLGLPAFSYSFFVIRNAKVAACI--
novel        PELKPRPLRAGRTLVIPPVTMGFFVVKNVNALACRYR
             * *  :***.* :* :*..: .***::*.:. **
Prim.cons.   P2L222PLR2G22L22P22222FFV22N2222AC2YR
```

Hu  TLARGLSPAFLRFGGKRTDFLQFQNLRNPAKSRGGPGPDYYLKNYEDDIVRSDVALDKQK
Mu  ------------FG--RGSCLMYR---------------------DIVRSDVALDKQK 130                                                              180

Hu  GCKIAQHPDVMLELQREKAAQMHLVLLKEQFSNTYSNLILTARSLDKLYNFADCSGLHLI
Mu  GCKIGQHPDVMLELQREKASRLSGS--SEGAILQYLQPHIN-RSLDKLYNFADCSGLHLI

190

Hu  FALNALRRNPNNSWXSSSALSLLKYSASKKYNISWELGEPNNYRTM
Mu  FALNALRRNPNNSWNSSSALSLLKYSASKKYNISW-----------
```

Figure 8b

```
HUMAN  301 TATCTCAAAA ACTATGAGGA TGACATTGTT CGAAGTGATG TTGCCTTAGA  350
MOUSE    6 ---------- ---------- -GACATTGTC CGGAGTGATG TTGCCTTGGA   56

360        370        380        390        400
HUMAN  351 TAAACAGAAA GGCTGCAAGA TTGCCCAGCA CCCTGATGTT ATGCTGGAGC  400
MOUSE   57 CAAGCAGAAA GGCTGTAAGA TTGCCCAGCA CCCTGATGTC ATGCTGGAGC  106

410        420        430        440        450
HUMAN  401 TCCAAGGGA GAAGGCAGCT CAGATGCATC TGGTTCTTTT AAAGGAGCAA  450
MOUSE  107 TCCAGAGAGA GAAGGCA-TC CAGAC-TGTC TGGTTCTTCT GAAGGAGCAA  156

460        470        480        490        500
HUMAN  451 TTCTCCAATA CTTACAGTAA TCTCATATTA ACAGCCAGGT CTCTAGACAA  500
MOUSE  157 TACTCCAATA CTTACAGTAA CCTCATATTA ACAG----GT CTCTAGACAA  206

510        520        530        540        550
HUMAN  501 ACTTTATAAC TTTGCTGATT GCTCTGGACT CCACCTGATA TTTGCTCTAA  550
MOUSE  207 ACTTTATAAC TTTGCTGATT GCTCTGGACT CCACCTGATA TTTGCTCTAA  256

560        570        580        590        600
HUMAN  551 ATGCACTGCG TCGTAATCCC AATAACTCCT GGANCAGTTC TAGTGCCCTG  600
MOUSE  257 ATGCACTGCG TCGTAATCCC AATAACTCCT GGAACAGTTC TAGTGCCCTG  306

610        620        630        640        650
HUMAN  601 AGTCTGTTGA AGTACAGCGC NAGCAAAAAG TACAACATTT CTTGGGAACT  650
MOUSE  307 AGCCTGTTGA AGTACAGTGC CAGCAAAAAG TACAACATTT CTTGGGAACT  356

660        670        680        690        700
HUMAN  651 GGGTAATAAC TATCGGACCA TGCATGGCCG GGCAGTAAAT GGCAGCCAGT  700
MOUSE  357 GGGTAAT--- ---------- ---------- ---------- ----------
```

HEPARANASE-LIKE POLYPEPTIDES

This application is a continuation of international application number PCT GB00/04963, filed Dec. 21, 2000.

BACKGROUND

The present invention relates to heparanase-like proteins and nucleotides that encode them.

Heparanase is an enzyme that can degrade heparan sulphate as well as heparin proteoglycans (HPG) and heparan sulphate proteoglycans (HSPG). Heparanase activity in mammalian cells is well known. The activity has been identified in various melanoma cells (Nakajima, et al., *Cancer Letters* 31:277-283, 1986), mammary adenocarcinoma cells (Parish, et al., *Int. J. Cancer,* 40:511-518, 1987), leukaemic cells (Yahalom, et al., *Leukemia Research* 12:711-717, 1988), prostate carcinoma cells (Kosir, et al., *J. Surg. Res.* 67:98-105, 1997), mast cells (Ogren and Lindahl, *J. Biol. Chem.* 250:2690-2697, 1975), macrophages (Savion, et al., *J. Cell. Physiol.* 130:85-92, 1987), mononuclear cells (Sewell, et al., *Biochem. J.* 264:777-783, 1989), neutrophils (Matzner, et al., 51:519-524, 1992, T-cells (Vettel et al., *Eur. J. Immunol.* 21:2247-2251, 1991), platelets (Haimovitz-Friedman, et al., *Blood* 78:789-796, 1991), endothelial cells (Godder, et al., *J. Cell Physiol.* 148:274-280, 1991), and placenta (Klein and von Figura, *BBRC* 73:569, 1976), and B cells.

Elevated heparanase activity has been documented in mobile, invasive cells, such as metastatic tumour cells. Examples include invasive melanoma (Nakajima et al *Science* 220:611 (1983)), lymphoma (Vlodavsky et al, *Cancer Res.* 43: 2704, (1983)), fibrosarcoma (Becker et al, *J. Natl. Cancer Inst.,* 77:417, (1986)), rhabdomyosarcoma (U.S. Pat. No. 4,882,318), mastocytoma, mammary adeno-carcinoma, leukaemia, and rheumatoid fibroblasts. Heparanase activity has also been documented in non-pathologic situations involving the migration of lymphocytes, neutrophils, macrophages, eosinophils and platelets (Vlodavsky et al., *Invasion Metastasis* 12:112-127, 1992). Heparanase activity is also implicated in inflammation (Hoogewerf *J. Biol Chem* 270:3268-3277 (1995); WO97/11684), wound healing (Whitelock et al, *J. Biol. Chem.* 271: 10079-10086, (1996)), angiogenesis (U.S. Pat. No. 5,567,417), inflammatory diseases such as arthritis (including rheumatoid- and osteo-), asthma, lupus erythematosus, allografts, as well as vascular restenosis, atherosclerosis, tumour growth and progression, fibro-proliferative disorders, Alzheimer's Disease (McBubbin et al *Biochem. J.* 256:775-783 (1999); Snow et al, *Neuron* 12: 219-234 (1996)) and several others. In general, it may be said that heparanase activity is present in mobile invasive cells in a variety of pathologies. Thus, inhibitors of heparanase are likely to be of great value in the treatment of these.

Further, inhibition of heparan sulphate degradation would inhibit the release of bound growth factors and other biologic response modifiers that would, if released, fuel the growth of adjacent tissues and provide a supportive environment for cell growth (Rapraeger et al., *Science* 252:1705-1708, 1991).

WO99/11798, WO99/21975, WO99/40207 and WO99/43830 all relate to nucleic acids encoding human heparanase, as well as polypeptides encoded by the nucleic acids.

SUMMARY OF THE INVENTION

The present inventors have identified a human heparanase-like protein which is present in at least three splice variants.

According to a first aspect of the present invention, there is provided a polypeptide which: comprises the amino acid sequence shown in FIG. 1 (Seq. ID No 2), starting at either residue 1 or residue 11; comprises the amino acid sequence shown in FIG. 2 (Seq. ID No 4), starting at either residue 1 or residue 11;comprises the amino acid sequence shown in FIG. 3 (Seq. ID No 6), starting at either residue 1 or residue 11; is a derivative having one or more amino acid substitutions, deletions or insertions relative to a substance as defined in a), b) or c) above; or is a fragment of a substance as defined in a), b), c) or d) above, which is at least five or ten amino acids long.

The present inventors have found a human homologue of heparanase which is present in three splice variants. There is considerable homology between the splice variants and the published sequence for human heparanase, and the peptides of the invention may demonstrate biochemical activity typical of an heparanase enzyme. The novel polypeptides of the present invention may exhibit activity that is similar to that of heparanase. Alternatively or additionally, the homologue may modulate the activity of endogenous heparanase activity (e.g. by having heparan binding domain fragments).

BRIEF DESCRIPTION OF THE DRAWINGS

FIG. 1 shows the nucleotide sequence (Seq. ID No 1) and predicted amino acid sequence (Seq. ID No 2) of the largest splice variant of the heparanase-like protein of the present invention, including 600 nucleotides of 5'UTR and 260 nucleotides of 3'UTR. The splice exon is shown bold and underlined, and the putative initiator sequence is underlined;

FIG. 2 shows the nucleotide sequence (Seq. ID No 3) and predicted amino acid sequence (Seq. ID No 4) of the mid-sized splice variant of the heparanase-like protein of the present invention, including 600 nucleotides of 5'UTR and 260 nucleotides of 3'UTR. The splice exon is shown in bold and underlined;

FIG. 3 shows the nucleotide sequence (Seq. ID No 5) and predicted amino acid sequence (Seq. ID No 6) of the smallest splice variant of the heparanase-like protein of the present invention, including 600 nucleotides of 5'UTR and 260 nucleotides of 3'UTR. The nucleotides in italics are the 9 PCR primers used to extend the sequence: for each region, two PCR primers are shown: hepa forward (F) or reverse (R) primers;

FIG. 4 shows alignment of the published heparanase protein ("heparanase") with the shortest splice variant (Seq. ID No 6) of the heparanase-like protein of the present invention ("novel"). The translated protein sequence is shown. *=identity, :=strongly similar, .=weakly similar, and -=spacing introduced to allow for best fit.

FIG. 8a shows an alignment of the amino acid sequence of the partial mouse heparanase-like sequence (Seq. ID No 8) with part of the long form of the human heparanase-like protein (Seq. ID No 2) of the present invention. Identities are shown in bold type. FIG. 8b shows an alignment of the nucleotide sequence of the mouse heparanase-like sequence (Seq. ID No 7) with part of the nucleotide sequence of the long form (Seq. ID No 1) of the human heparanase-like protein of the present invention.

DETAILED DESCRIPTION OF THE INVENTION

Figure 5:
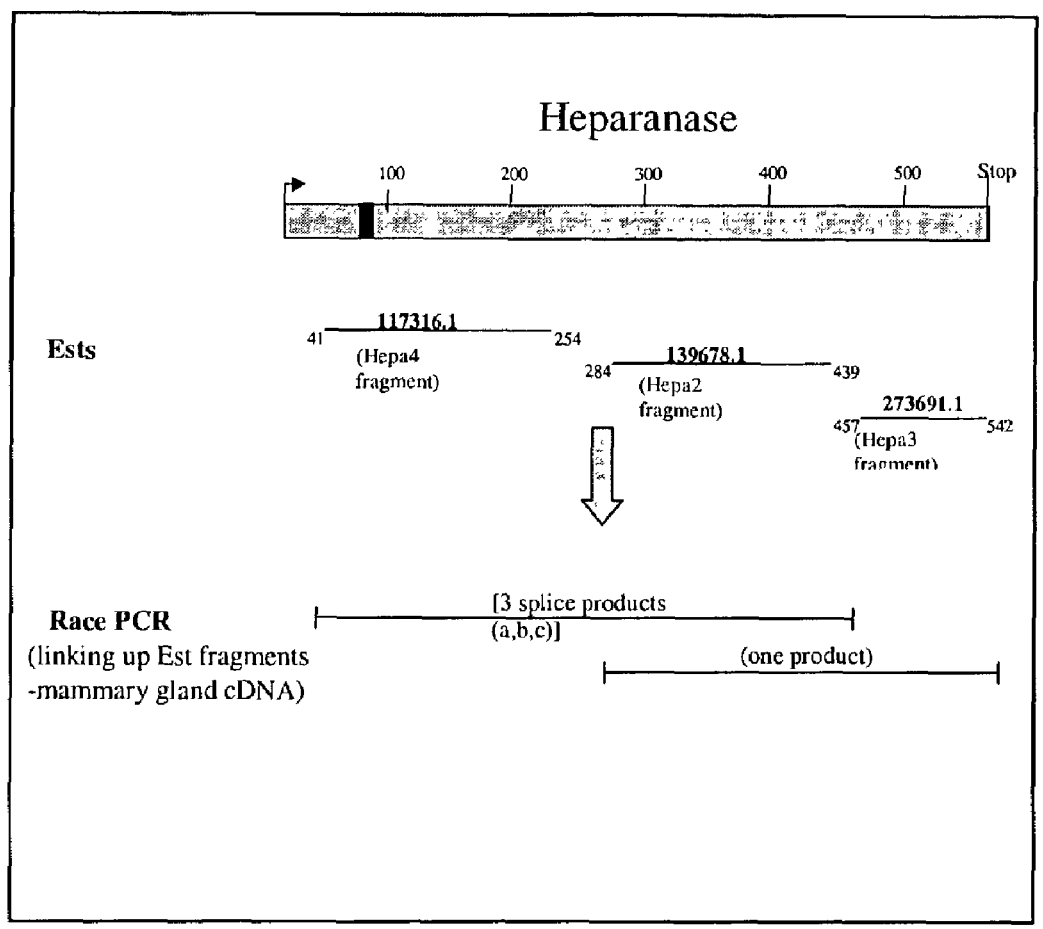
FIG. 5 shows the general strategy used to identify the heparanase-like proteins of the present invention.

The proteins or polypeptides of the present invention are referred to as Hpa2 or Hpa2-related proteins. Hpa2 refers to a protein having the amino acid sequence of FIG. 1, 2 or 3 (Seq. ID No 2, 4 or 6), starting at residue 1, 2, 11 or 12. Hpa2-related proteins are Hpa2 derivatives, including analogues, orthologues and homologues, Hpa2 fusion proteins, fragments, isoforms, variants or fragments of any of the preceding.

The skilled person is able to determine whether or not any given polypeptide has the activity of heparanase, for example using any known assay for heparanase activity. Haimovitz-Friedman et al (*Blood* 78: 789-796, 1991) describe an assay for heparanase activity that involves culturing endothelial cells in radiolabelled $^{35}SO_4$ to produce radio-labelled heparan sulphate proteoglycans. The cells are removed to leave the extracellular deposited matrix that contains the $^{35}$S-HSPG, the putative heparanase is added and activity is detected by passing the supernatant from the radiolabelled extracellular matrix over a gel filtration column. Changes in the size of the radiolabelled material indicate that HSPG degradation has taken place. An alternative assay is described by Nakajima et al (*Anal. Biochem.* 196: 162-171, 1986). In this assay, melanoma heparanase activity is assayed by radiolabelling heparan sulphate from bovine lung with [$^{14}$C]-acetic anhydride. Free amino groups of the [$^{14}$C]-heparan sulphate are acetylated and the reducing termini aminated. The [$^{14}$C]-heparan sulphate is chemically coupled to an agarose support via the introduced amine groups on the reducing termini to provide a solid phase substrate. An indirect assay for heparanase activity utilises the ability of heparin to interfere with the colour development between a protein and Coomassie brilliant blue dye (Khan & Newman, *Anal. Biochem*, 196: 373-376, 1991). Heparanase activity is detected by the loss of this interference. WO99/43830 also describes an assay for heparanase activity.

Polypeptides of the present invention may be in any appropriate form. They may be isolated or recombinant, and may be fused to other moieties. They may be provided in substantially pure form. Thus, a polypeptide of the present invention may be provided in a composition in which it is the predominant component present (i.e. it is present at a level of at least 50%; preferably at least 75%, at least 90%, or at least 95%; when determined on a weight/weight basis excluding solvents or carriers).

In a preferred embodiment, the protein of the present invention comprise at least 13, at least 15, at least 20, at least 25, or at least 30 consecutive amino acids of the amino acid sequence depicted in FIG. 1 (Seq. ID No 2).

The Hpa2 or Hpa2-related protein of the present invention may exist as two polypeptide chains, one being exactly or about the amino terminal 7, 8, 9, 10, 11, 12 or 13 kD of the full length Hpa2 or Hpa2-related protein, the second being the remaining carboxy terminal of the protein. Optionally, the second, carboxy terminal polypeptide chain may have exactly or about 4, 5, 6, 7, 8 or 9 kD of its amino terminus removed. The two polypeptide chains may be produced separately, or from a single transcript. When produced from a single transcript, the resulting full length polypeptide is further processed to produce the two polypeptides.

In order to more fully appreciate the present invention, polypeptides within the scope of a)-e) above will now be discussed in greater detail.

Polypeptides within the Scope of a), b) or c)

A polypeptide within the scope of a), b) or c) may consist of the particular amino acid sequence given in FIG. 1, 2 or 3 (Seq. ID No 2, 4 or 6), respectively or may have an additional N-terminal and/or an additional C-terminal amino acid sequence relative to the sequence given in FIG. 1, 2 or 3 (Seq. ID No 2, 4 or 6) respectively.

The term "fusion protein" as used herein refers to a polypeptide that comprises (i) an amino acid sequence of Hpa2 or an Hpa2-related polypeptide and (ii) an amino acid sequence of a heterologous polypeptide (i.e., a non-Hpa2, non-Hpa2-related polypeptide).

Additional N-terminal or C-terminal sequences may be provided for various reasons. Techniques for providing such additional sequences are well known in the art. Additional sequences may be provided in order to alter the characteristics of a particular polypeptide. This can be useful in improving expression or regulation of expression in particular expression systems. For example, an additional sequence may provide some protection against proteolytic cleavage. This has been done for the hormone Somatostatin by fusing it at its N-terminus to part of the β galactosidase enzyme (Itakwa et al., *Science* 198: 105-63 (1977)). Additional sequences can also be useful in altering the properties of a polypeptide to aid in identification or purification. For example, a fusion protein may be provided in which a polypeptide is linked to a moiety capable of being isolated by affinity chromatography. The moiety may be an antigen or an epitope and the affinity column may comprise immobilised antibodies or immobilised antibody fragments which bind to said antigen or epitope (desirably with a high degree of specificity). The fusion protein can usually be eluted from the column by addition of an appropriate buffer. Additional N-terminal or C-terminal sequences may, however, be present simply as a result of a particular technique used to obtain a polypeptide of the present invention and need not provide any particular advantageous characteristic to the polypeptide of the present invention. Such polypeptide are within the scope of the present invention. Whatever additional N-terminal or C-terminal sequence is present, it is preferred that the resultant polypeptide has at least a substantial proportion of the activity of the polypeptide having the amino acid sequence shown in FIG. 1, 2 or 3 (Seq. ID No 2, 4 or 6). The term "at least a substantial proportion of activity" when used herein means at least 50% of the activity of a given substance (preferably at least 75% of said activity, more preferably at least 90% of said activity, and most preferably the same level of activity or a greater level of activity).

Also included within the scope of a), b) and c) are isoforms. The term "isoform" as used herein refers to variants of a polypeptide that are encoded by the same gene, but that differ in their pI or MW, or both. Such isoforms can differ in their amino acid composition (e.g. as a result of alternative mRNA or pre-mRNA processing, e.g. alternative splicing or limited proteolysis) and in addition, or in the alternative, may arise from differential post-translational modification (e.g., glycosylation, acylation, phosphorylation).

Polypeptides within the Scope of d)

Turning now to the polypeptides defined in d) above, it will be appreciated by the person skilled in the art that these polypeptides are analogues, homologues, orthologues and variants of the polypeptide given in a), b) or c) above. Such polypeptides may or may not have at least a substantial proportion of the activity of the polypeptide having the amino acid sequence shown in FIG. 1, 2 or 3 (Seq. ID No 2, 4 or 6).

The term "Hpa2 analogue" as used herein refers to a polypeptide that possesses similar or identical function(s) as Hpa2 but need not necessarily comprise an amino acid sequence that is similar or identical to the amino acid sequence of Hpa2, or possess a structure that is similar or identical to that of Hpa2. As used herein, an amino acid sequence of a polypeptide is "similar" to that of Hpa2 if it satisfies at least one of the following criteria: (a) the polypeptide has an amino acid sequence of at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to an amino acid sequence of Hpa2; (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of Hpa2; or (c) the polypeptide is encoded by a nucleotide sequence of at least 10 nucleotides (more preferably, at least 15 nucleotides, at least 20 nucleotides, at least 25 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, or at least 150 nucleotides) that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence, or a portion thereof, encoding Hpa2. As used herein, a polypeptide with "similar structure" to that of Hpa2 refers to a polypeptide that has a similar secondary, tertiary or quarternary structure as that of Hpa2. The structure of a polypeptide can be determined by methods known to those skilled in the art, including but not limited to, X-ray crystallography, nuclear magnetic resonance, and crystallographic electron microscopy.

The term "homologue" as used herein refers to a polypeptide that comprises an amino acid sequence similar to that of Hpa2, but does not necessarily possess a similar or identical function as Hpa2.

The term "orthologue" as used herein refers to a non-human polypeptide that (i) comprises an amino acid sequence similar to that of Hpa2 and (ii) possesses a similar or identical function to that of Hpa2.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. The NBLAST and XBLAST programs of Altschul, et al. (1990) *J. Mol. Biol.* 215:403-410 have incorporated such an algorithm. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov.

Another example of a mathematical algorithm utilized for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) *Comput. Appl. Biosci.*, 10 :3-5; and FASTA described in Pearson and Lipman (1988) *Proc. Natl. Acad. Sci.* 85:2444-8. Within FASTA, ktup is a control option that sets the sensitivity and speed of the search.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signalling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198: 1056; Ike et al. (1983) *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811-7815; Delgrave et al. (1993) *Protein Engineering* 6(3):327-331).

Alterations in the amino acid sequence of a protein can occur which do not affect the function of a protein. These include amino acid deletions, insertions and substitutions and can result from alternative splicing and/or the presence of multiple translation start sites and stop sites. Polymorphisms may arise as a result of the infidelity of the translation process. Thus changes in amino acid sequence may be tolerated which do not affect the protein's function.

The skilled person will appreciate that various changes can often be made to the amino acid sequence of a polypeptide which has a particular activity to produce variants (sometimes known as "muteins") having at least a proportion of said activity, and preferably having a substantial proportion of said activity. Such variants of the polypeptides described in a), b) and c) above are within the scope of the present invention and are discussed in greater detail below. They include allelic and non-allelic variants.

An example of a variant of the present invention is a polypeptide as defined in a), b) or c) above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus, the amino acids glycine, alanine, valine, leucine and isoleucine can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic).

Other amino acids which can often be substituted for one another include:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Substitutions of this nature are often referred to as "conservative" or "semi-conservative" amino acid substitutions.

Amino acid deletions or insertions may also be made relative to the amino acid sequence given in a), b) or c) above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence given in a), b) or c) above can also be made. This may be done to alter the properties of a polypeptide of the present invention (e.g. to assist in identification, purification or expression, as explained above in relation to fusion proteins).

Amino acid changes relative to the sequence given in a), b) or c) above can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present. Whatever amino acid changes are made (whether by means of substitution, insertion or deletion), preferred polypeptides of the present invention have at least 50% sequence identity with a polypeptide as defined in a), b) or c) above, more preferably the degree of sequence identity is at least 75%. Sequence identities of at least 90% or at least 95% are most preferred.

The term identity can be used to describe the similarity between two polypeptide sequences. The degree of amino acid sequence identity can be calculated using a program such as "bestfit" (Smith and Waterman, Advances in Applied Mathematics, 482-489 (1981)) to find the best segment of similarity between any two sequences. The alignment is based on maximising the score achieved using a matrix of amino acid similarities, such as that described by Schwarz and Dayhof (1979) Atlas of Protein Sequence and Structure, Dayhof, M. O., Ed pp 353-358.

A software package well known in the art for carrying out this procedure is the CLUSTAL program. It compares the amino acid sequences of two polypeptides and finds the optimal alignment by inserting spaces in either sequence as appropriate. The amino acid identity or similarity (identity plus conservation of amino acid type) for an optimal alignment can also be calculated using a software package such as BLASTx. This program aligns the largest stretch of similar sequence and assigns a value to the fit. For any one pattern comparison, several regions of similarity may be found, each having a different score. One skilled in the art will appreciate that two polypeptides of different lengths may be compared over the entire length of the longer fragment. Alternatively small regions may be compared. Normally sequences of the same length are compared for a useful comparison to be made.

Where high degrees of sequence identity are present there will be relatively few differences in amino acid sequence. Thus for example they may be less than 20, less than 10, or even less than 5 differences.

Polypeptides within the Scope of e)

As discussed supra, it is often advantageous to reduce the length of a polypeptide, provided that the resultant reduced length polypeptide still has a desired activity or can give rise to useful antibodies. Feature e) of the present invention therefore covers fragments of polypeptides a), b), c) or d) above.

The term "fragment" as used herein refers to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of Hpa2 or an Hpa related peptide may or may not possess a functional activity of Hpa2.

The skilled person can determine whether or not a particular fragment has activity using the techniques disclosed above. Preferred fragments are at least 10 amino acids long. They may be at least 20, at least 50 or at least 100 amino acids long. One embodiment provides a protein comprising the amino acid sequence shown in FIG. 1, 2 or 3 (Seq. ID No 2, 4 or 6), starting at either residue 2 or residue 12. Another embodiment provides polypeptides which start at amino acid residue 43 of the respective sequences shown in FIGS. 1, 2 and 3 (Seq. ID No 2, 4 or 6), where the first methionine residue shown is residue 1.

Therapeutic polypeptides of the present invention may be used in the treatment of a human or non-human animal. The treatment may be prophylactic or may be in respect of an existing condition. For example, polypeptides of the invention may be used in the treatment of any disease/disorder resulting from a lack/shortage of heparanase. In addition, they may be used for the degradation of heparin or for blocking heparin's anticoagulant activity during or post surgery (see Freed et al, *Ann. Biomed. Eng.* 21: 67-76, 1993). Alternatively, they may be used to modulate the activity of endogenous heparanase.

Thus, in a further aspect, the present invention provides a pharmaceutical composition comprising a polypeptide of the first aspect of the invention and a pharmaceutically acceptable carrier. The polypeptides of the present invention may also be used in the manufacture of a medicament for the treatment of one or more of the above-mentioned diseases/disorders.

The medicament will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions, oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulisers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilised) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used. This dosage may be repeated as often as appropriate. If side effects develop the amount and/or frequency of the dosage can be reduced, in accordance with normal clinical practice.

In addition to the uses discussed above in relation to treatments, polypeptides of the present invention can be used in diagnosis. For example, expression of the polypeptide may be associated with a condition, or an increased risk of contracting a condition.

Polypeptides of the present invention can also be used in research. For example, they can be used in screening for agents that modulate the activity of the polypeptides of the present invention.

Thus, according to a further aspect of the invention, there is provided a method for the identification of an agent that modulates the activity of the polypeptides of the invention, comprising comparing the activity of a polypeptide of the invention in the presence of a test agent with the activity of a polypeptide of the invention in the absence of the test agent.

The invention provides methods for identifying agents (e.g., candidate compounds or test compounds) that bind to Hpa2 or an Hpa2-related protein or have a stimulatory or inhibitory effect on the expression or activity of Hpa2 or an Hpa2-related protein. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g., presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310), each of which is incorporated herein in its entirety by reference.

In one embodiment, agents that interact with (i.e., bind to) Hpa2 or an Hpa2-related protein are identified in a cell-based assay system. In accordance with this embodiment, cells expressing Hpa2 or an Hpa2-related protein are contacted with a candidate compound or a control compound and the ability of the candidate compound to interact with Hpa2 or an Hpa2-related protein is determined. If desired, this assay may be used to screen a plurality (e.g. a library) of candidate compounds. The cell, for example, can be of prokaryotic origin (e.g., E. coli) or eukaryotic origin (e.g., yeast or mammalian). Further, the cells can express Hpa2 or an Hpa2-related protein endogenously or be genetically engineered to express Hpa2 or an Hpa2-related protein. In certain instances, Hpa2 or an Hpa2-related protein, or the candidate compound is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between Hpa2 or an Hpa2-related protein and a candidate compound. The ability of the candidate compound to interact directly or indirectly with Hpa2 or an Hpa2-related protein can be determined by methods known to those of skill in the art. For example, the interaction between a candidate compound and Hpa2 or an Hpa2-related protein can be determined by flow cytometry, a scintillation assay, immunoprecipitation or western blot analysis.

In another embodiment, agents that interact with (i.e., bind to) Hpa2 or an Hpa2-related protein are identified in a cell-free assay system. In accordance with this embodiment, a native or recombinant Hpa2 or fragment thereof, or a native or recombinant Hpa2-related polypeptide or fragment thereof is contacted with a candidate compound or a control compound and the ability of the candidate compound to interact with Hpa2 or Hpa2-related polypeptide is determined. If desired, this assay may be used to screen a plurality (e.g. a library) of candidate compounds. Preferably, Hpa2 or an Hpa2-related protein is first immobilized, by, for example, contacting Hpa2 or an Hpa2-related protein with an immobilized antibody which specifically recognizes and binds it, or by contacting a purified preparation of Hpa2 or an Hpa2-related protein with a surface designed to bind proteins. Hpa2 or an Hpa2-related protein may be partially or completely purified (e.g., partially or completely free of other polypeptides) or part of a cell lysate. Further, Hpa2 or an Hpa2-related protein may be a fusion protein comprising the Hpa2 or a biologically active portion thereof, or Hpa2-related polypeptide and a domain such as glutathionine-S-transferase. Alternatively, Hpa2 or an Hpa2-related protein can be biotinylated using techniques well known to those of skill in the art (e.g., biotinylation kit, Pierce Chemicals; Rockford, Ill.). The ability of the candidate compound to interact with Hpa2 or an Hpa2-related protein can be can be determined by methods known to those of skill in the art.

In another embodiment, a cell-based assay system is used to identify agents that bind to or modulate the activity of a protein, such as an enzyme, or a biologically active portion thereof, which is responsible for the production or degradation of Hpa2 or an Hpa2-related protein or is responsible for the post-translational modification of Hpa2 or an Hpa2-related protein. In a primary screen, a plurality (e.g., a library) of compounds are contacted with cells that naturally or recombinantly express: (i) Hpa2 or an Hpa2-related protein, or a biologically active fragment of any of the foregoing; and (ii) a protein that is responsible for processing of Hpa2 or an Hpa2-related protein in order to identify compounds that modulate the production, degradation, or post-translational modification of Hpa2 or an Hpa2-related protein. If desired, compounds identified in the primary screen can then be assayed in a secondary screen against cells naturally or recombinantly expressing the specific Hpa2 of interest. The ability of the candidate compound to modulate the production, degradation or post-translational modification of Hpa2 or an Hpa2-related protein can be determined by methods known to those of skill in the art, including without limitation, flow cytometry, a scintillation assay, immunoprecipitation and western blot analysis.

In another embodiment, agents that competitively interact with (i.e., bind to) Hpa2 or an Hpa2-related protein are identified in a competitive binding assay. In accordance with this embodiment, cells expressing Hpa2 or an Hpa2-related protein are contacted with a candidate compound and a compound known to interact with Hpa2 or an Hpa2-related protein; the ability of the candidate compound to competitively interact with Hpa2 or an Hpa2-related protein is then determined. Alternatively, agents that competitively interact with (i.e., bind to) Hpa2 or an Hpa2-related protein are identified in a cell-free assay system by contacting Hpa2 or an Hpa2-related protein with a candidate compound and a compound known to interact with the Hpa2 or Hpa2-related polypeptide. As stated above, the ability of the candidate compound to interact with Hpa2 or an Hpa2-related protein can be determined by methods known to those of skill in the art. These assays, whether cell-based or cell-free, can be used to screen a plurality (e.g., a library) of candidate compounds.

In another embodiment, agents that modulate (i.e., upregulate or downregulate) the expression of Hpa2 or an Hpa2-related protein are identified by contacting cells (e.g., cells of prokaryotic origin or eukaryotic origin) expressing Hpa2 or an Hpa2-related protein with a candidate compound or a control compound (e.g., phosphate buffered saline (PBS)) and determining the expression of Hpa2 or an Hpa2-related protein, mRNA encoding Hpa2, or mRNA encoding the Hpa2-related polypeptide. The level of expression of a selected Hpa2, Hpa2-related polypeptide, mRNA encoding Hpa2, or mRNA encoding the Hpa2-related polypeptide in the presence of the candidate compound is compared to the level of expression of Hpa2, Hpa2-related polypeptide, mRNA encoding Hpa2, or mRNA encoding the Hpa2-related polypeptide in the absence of the candidate compound (e.g., in the presence of a control compound). The candidate compound can then be identified as a modulator of the expression of Hpa2 or Hpa2-related polypeptide based on this comparison. For example, when expression of Hpa2 or mRNA is significantly greater in the presence of the candidate compound than in its absence, the candidate compound is identified as a stimulator of expression of Hpa2 or mRNA. Alternatively, when expression of Hpa2 or mRNA is significantly less in the presence of the candidate compound than in its absence, the candidate compound is identified as an inhibitor of the expression of Hpa2 or mRNA. The level of expression of Hpa2 or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of Hpa2 or an Hpa2-related polypeptide are identified by contacting a preparation containing Hpa2 or an Hpa2-related polypeptide, or cells (e.g., prokaryotic or eukaryotic cells) expressing Hpa2 or an Hpa2-related polypeptide with a test compound or a control compound and determining the ability of the test compound to modulate (e.g., stimulate or inhibit) the activity of Hpa2 or an Hpa2-related polypeptide. The activity of Hpa2 or an Hpa2-related polypeptide can be assessed by detecting the enzymatic activity of Hpa2 or the Hpa2-related protein the target on a suitable substrate, detecting the induction of a reporter gene (e.g., a regulatory element that is responsive to Hpa2 or an Hpa2-related polypeptide and is operably linked to a nucleic acid encoding a detectable marker, e.g., luciferase), or detecting a cellular response, for example, cellular differentiation, or cell proliferation. Based on the present description, techniques known to those of skill in the art can be used for measuring these activities. The candidate compound can then be identified as a modulator of the activity of Hpa2 or Hpa2-related polypeptide by comparing the effects of the candidate compound to the control compound. Suitable control compounds include phosphate buffered saline (PBS) and normal saline (NS).

In another embodiment, agents that modulate (i.e., upregulate or downregulate) the expression, activity or both the expression and activity of Hpa2 or Hpa2-related polypeptide are identified in an animal model. Examples of suitable animals include, but are not limited to, mice, rats, rabbits, monkeys, guinea pigs, dogs and cats. In accordance with this embodiment, the test compound or a control compound is administered (e.g., orally, rectally or parenterally such as intraperitoneally or intravenously) to a suitable animal and the effect on the expression, activity or both expression and activity of Hpa2 or an Hpa2-related polypeptide is determined. Changes in the expression of Hpa2 or an Hpa2-related polypeptide can be assessed by the methods outlined above.

In yet another embodiment, Hpa2 or an Hpa2-related polypeptide is used as a "bait protein" in a two-hybrid assay or three hybrid assay to identify other proteins that bind to or interact with Hpa2 or an Hpa2-related polypeptide (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by Hpa2 or an Hpa2-related protein of the inventions as, for example, upstream or downstream elements of a signaling pathway involving Hpa2 or an Hpa2-related protein. Scientific publications describing suitable assays for detecting or quantifying heparanase activity are listed herein.

This invention further provides novel agents identified by the above-described screening assays and uses thereof for treatments as described herein Agents that increase or enhance the activity of the polypeptides of the invention may be used for the degradation of heparin or for blocking heparin's anticoagulant activity during or post surgery (see Freed et al, *Ann. Biomed. Eng.* 21: 67-76, 1993), and in the treatment/prophylaxis of any disease/disorder resulting from a lack/shortage of heparanase. The invention therefore also provides the use of an agent which increases or enhances the activity of the polypeptides of the invention in the manufacture of a medicament for the treatment of one or more of these conditions.

As mentioned above, heparanase activity is present in mobile invasive cells in a variety of pathologies. Heparanase activity is also implicated in cancer (in particular metastasis), CNS and neurodegenerative diseases, inflammation and in cardiovascular diseases such as restenosis following angioplasty and atherosclerosis. Agents that decrease or inhibit the activity of the polypeptides of the present invention may be useful in the treatment and/or prophylaxis of, for example: autoimmune diseases such as psoriasis, lupus erythematosus, allografts; inflammatory diseases such as arthritis (including rheumatoid- and osteo-); asthma; vascular restenosis; atherosclerosis; preventing tumour growth and progression; fibro-proliferative disorders; Alzheimer's Disease; diabetic retinopathy. In addition, they may be used in wound healing, in blocking angiogenesis (see U.S. Pat. No. 5,567,417) or inflammation (see WO97/11684). The invention therefore also provides the use of an agent which decreases or inhibits the activity of the polypeptides of the invention in the manufacture of a medicament for the treatment of one or more of these conditions. Examples of such agents include maltohexaose sulfate, PI88 and calcium spirulan.

One further use of the polypeptides of the present invention is in raising or selecting antibodies. The present invention therefore includes antibodies which bind to a polypeptide of the present invention or to a fragment of such a polypeptide. Preferred antibodies bind specifically to polypeptides of the present invention so that they can be used to purify and/or inhibit the activity of such polypeptides. The antibodies may be monoclonal or polyclonal.

An Hpa2 or Hpa2-related protein may be used as an immunogen to generate antibodies which immunospecifically bind such an immunogen. Such immunogens can be isolated by any convenient means, including the methods described above. Antibodies of the invention include, but are not limited to polyclonal, monoclonal, bispecific, humanized or chimeric antibodies, single chain antibodies, Fab fragments and F(ab') fragments, fragments produced by a Fab expression library, anti-idiotypic (anti-Id) antibodies, and epitope-binding fragments of any of the above. The term "antibody" as used herein refers to immunoglobulin molecules and immunologically active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

In one embodiment of the invention, antibodies to a specific domain of Hpa2 or an Hpa2-related protein are produced. In a specific embodiment, hydrophilic fragments of Hpa2 or an Hpa2-related protein are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of Hpa2 or an Hpa2-related protein, one may assay generated hybridomas for a product which binds to a fragment of Hpa2 or an Hpa2-related protein containing such domain.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to Hpa2 or an Hpa2-related protein. In a particular embodiment, rabbit polyclonal antibodies to an epitope of Hpa2 or an Hpa2-related polypeptide can be obtained. For example, for the production of polyclonal or monoclonal antibodies, various host animals can be immunized by injection with the native or a synthetic (e.g., recombinant) version of Hpa2 or an Hpa2-related polypeptide, or a fragment of an Hpa2-related polypeptide, including but not limited to rabbits, mice, rats, etc.

Various adjuvants may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or corynebacterium parvum. Additional adjuvants are also well known in the art.

For preparation of monoclonal antibodies (mAbs) directed toward Hpa2 or an Hpa2-related protein, a fragment of Hpa2 or an Hpa2-related protein, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g., human-mouse chimeras). A chimeric antibody is a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125, 023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314: 446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060.

Completely human antibodies are particularly desirable for therapeutic treatment of human subjects. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of an Hpa2 of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633, 425; 5,569,825; 5,661,016; and 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Bio/technology 12:899-903).

The antibodies of the present invention can also be generated using various phage display methods known in the art. In phage display methods, functional antibody domains are displayed on the surface of phage particles which carry the polynucleotide sequences encoding them. In a particular, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427, 908; 5,750,753; 5,821,047; 5,571,698; 5,427,908; 5,516, 637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CHI) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology,1986, 121: 210.

The invention provides functionally active fragments, derivatives or analogs of the anti-Hpa2 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CHI domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g., a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are either modified, i.e, by the covalent attachment of any type of molecule as long as such covalent attachment that does not impair immunospecific binding. For example, but not by way of limitation, the derivatives and analogs of the immunoglobulins include those that have been further modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of the Hpa2 of the invention, e.g., for imaging these proteins, measuring levels thereof in appropriate physiological samples, in diagnostic methods, etc.

The antibodies of the invention can be produced by any method known in the art for the synthesis of antibodies, in particular, by chemical synthesis or by recombinant expression, and are preferably produced by recombinant expression technique. Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR. Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g., PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCT based methods, etc.

In addition, techniques developed for the production of "chimeric antibodies" (Morrison et al., 1984, Proc. Natl. Acad. Sci. 81:851-855; Neuberger et al., 1984, *Nature* 312:604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g., humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, 2d Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention. The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus is an effective expression system for antibodies (Foecking et al., 198, Gene 45:101; Cockett et al., 1990, Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the *vaccinia* virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system) may be utilized.

As discussed above, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein.

For long-term, high-yield production of recombinant antibodies, stable expression is preferred. For example, cells lines that stably express an antibody of interest can be produced by transfecting the cells with an expression vector comprising the nucleotide sequence of the antibody and the nucleotide sequence of a selectable (e.g., neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, *The use of vectors based on gene amplification for the expression of cloned genes in mammalian cells in DNA cloning*, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g., ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a *vaccinia* recombination plasmid such that the open reading frame of the gene is translationally fused to an amino-terminal tag consisting of six histidine residues. The tag serves as a matrix binding domain for the fusion protein. Extracts from cells infected with recombinant *vaccinia* virus are loaded onto Ni2+ nitriloacetic acid-agarose columns and histidine-tagged proteins are selectively eluted with imidazole-containing buffers.

In a preferred embodiment, anti-Hpa2 or Hpa2-related protein antibodies or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Anti-Hpa2 or Hpa2-related protein antibodies or fragments thereof can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980. An antibody with or without a therapeutic moiety conjugated to it can be used as a therapeutic that is administered alone or in combination with cytotoxic factor(s) and/or cytokine(s).

Polyclonal antibodies can be raised by stimulating their production in a suitable animal host (e.g. a chicken, mouse, rat, guinea pig, rabbit, sheep, goat or monkey) when the polypeptide of the present invention is injected into the animal. If necessary, an adjuvant may be administered together with the polypeptide of the present invention. The antibodies can then be purified by virtue of their binding to a polypeptide of the present invention.

Monoclonal antibodies can be produced from hybridomas. These can be formed by fusing myeloma cells and spleen cells which produce the desired antibody in order to form an immortal cell line. This is the well known Kohler & Milstein technique (*Nature* 256 52-55 (1975)). Techniques for producing monoclonal and polyclonal antibodies which bind to a particular protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to polypeptides of the present invention. Thus the present invention includes antibody fragments and synthetic constructs. Examples of antibody fragments and synthetic constructs are given by Dougall et al in *Tibtech* 12 372-379 (September 1994).

Antibody fragments include, for example, Fab, F(ab')$_2$ and Fv fragments (see Roitt et al [supra]). Fv fragments can be modified to produce a synthetic construct known as a single chain Fv (scFv) molecule. This includes a peptide linker covalently joining $V_h$ and $V_l$ regions which contribute to the stability of the molecule.

Other synthetic constructs include CDR peptides. These are synthetic peptides comprising antigen binding determinants. Peptide mimetics may also be used. These molecules are usually conformationally restricted organic rings which mimic the structure of a CDR loop and which include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions.

Synthetic constructs also include molecules comprising a covalently linked moiety which provides the molecule with some desirable property in addition to antigen binding. For example, the moiety may be a label (e.g. a fluorescent or radioactive label) or a pharmaceutically active agent.

Figure 7:
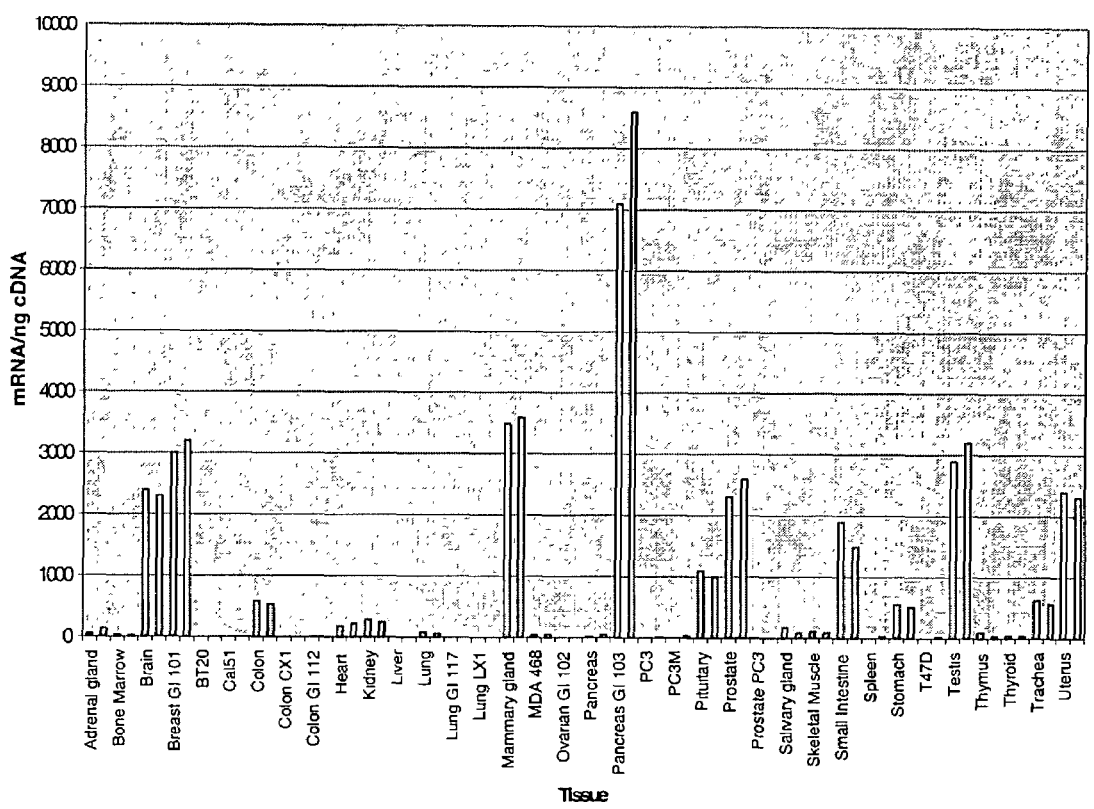
FIG. 7 is a graph showing the expression of mRNA, relative to cDNA, for the heparanase-like protein of the present invention in a variety of tissues, normal and tumour, and cell lines.

The antibodies or derivatives thereof of the present invention have a wide variety of uses. They can be used in purification and/or identification of the substances of the present invention. Thus they may be used in diagnosis. They can be provided in the form of a kit for screening for the polypeptides of the present invention. The invention also provides the use of such an antibody in the manufacture of a medicament for the treatment of conditions associated with raised activity of heparanase, such as cancer (in particular metastasis), CNS and neurodegenerative diseases, inflammation and in cardiovascular diseases such as restenosis following angioplasty and atherosclerosis. From the expression data available (see FIG. 7) it appears that pancreatic cancer may be a condition which could be treated with antibodies raised to the polypeptides of the present invention.

The present invention also provides antigenic/immunogenic fragments of the polypeptides of the invention. Examples of such fragments are:

```
QPIRIYSRASLYGPNIGRPRKNV      (Seq. ID No 9)

DTLSDQIRKIQKVVNTYTPGKKIW     (Seq. ID No 10)

AVHVAGLQRKPRPGRVIRDKLRIYA    (Seq. ID No 11)
```

The fragments can be provided alone, as a purified or isolated preparation, or as part of a mixture with one another.

The invention also provides an antigen composition comprising one or more of such fragments, and a kit for use in the detection of the heparanase-like protein of the present invention, which kit comprises one or more such fragments. In addition, the fragments can be used to induce an immune response against the heparanase-like protein of the present invention. Thus, the invention also provides the use of such fragments in medicine.

The present invention also provides a composition capable of eliciting an immune response in a subject, which composition comprises such a fragment. Suitably, the composition will be a vaccine composition, optionally comprising one or more suitable adjuvants. Such a vaccine composition may be either a prophylactic or therapeutic vaccine composition. The vaccine compositions of the invention can include one or more adjuvants. Examples well-known in the art include inorganic gels, such as aluminium hydroxide, and water-in-oil emulsions, such as incomplete Freund's adjuvant. Other useful adjuvants will be well known to the skilled person.

The present invention also provides: the use of such a fragment in the preparation of an immunogenic composition, preferably a vaccine; and the use of such an immunogenic composition in inducing an immune response in a subject.

Hpa2 or Hpa2-related proteins can be detected in an immunoassay. In one embodiment, an immunoassay is performed by contacting a sample from a subject to be tested with an anti-Hpa2 antibody under conditions such that immunospecific binding can occur if the Hpa2 is present, and detecting or measuring the amount of any immunospecific binding by the antibody. Anti-Hpa2 antibodies can be produced by the methods and techniques taught herein.

Hpa2 can be probed in suitable assays that include, without limitation, competitive and non-competitive assay systems using techniques such as western blots and "sandwich" immunoassays using antibodies against a polypeptide of the present invention as described herein.

In one embodiment, binding of antibody in tissue sections can be used to detect aberrant Hpa2 localization or an aberrant level of Hpa2. In a specific embodiment, an antibody to an Hpa2 can be used to assay a tissue sample from a subject for the level of the Hpa2 where an aberrant level of Hpa2 is indicative of a condition associated with raised activity of heparanase, such as cancer (in particular metastasis), CNS and neurodegenerative diseases, inflammation and in cardiovascular diseases such as restenosis following angioplasty and atherosclerosis. In a preferred embodiment, pancreatic cancer is detected with antibodies raised to the polypeptides of the present invention. As used herein, an "aberrant level" means a level that is increased or decreased compared with the level in a subject free the concerned disease condition or a reference level. If desired, the comparison can be performed with a matched sample from the same subject, taken from a portion of the body not affected by the condition. Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, Hpa2 or an Hpa2-related protein can be detected in a fluid sample (e.g., CSF, blood, urine, or tissue homogenate) by means of a two-step sandwich assay. In the first step, a capture reagent (e.g., an anti-Hpa2 antibody) is used to capture the Hpa2. The capture reagent can optionally be immobilized on a solid phase. In the second step, a directly or indirectly labeled detection reagent is used to detect the captured Hpa2.

If desired, a gene encoding an Hpa2, a related gene, or related nucleic acid sequences or subsequences, including complementary sequences, can also be used in hybridization assays. A nucleotide encoding an Hpa2, or subsequences thereof comprising at least 8 nucleotides, preferably at least 12 nucleotides, and most preferably at least 15 nucleotides can be used as a hybridization probe. Preferably, the probe used is one that does not hybridize under the chosen conditions to sequences encoding heparanase. Hybridization assays can be used for detection, prognosis, diagnosis, or monitoring of conditions, disorders, or disease states, associated with aberrant expression of genes encoding Hpa2, or for differential diagnosis of subjects with signs or symptoms suggestive of a condition associated with raised activity of heparanase. In particular, such a hybridization assay can be carried out by a method comprising contacting a subject's sample containing nucleic acid with a nucleic acid probe capable of hybridizing to a DNA or RNA that encodes an Hpa2, under conditions such that hybridization can occur, and detecting or measuring any resulting hybridization. Nucleotides can be used for therapy of subjects having a condition associated with raised activity of heparanase.

The invention also provides diagnostic kits, comprising an anti-Hpa2 antibody. In addition, such a kit may optionally comprise one or more of the following: (1) instructions for using the anti-Hpa2 antibody for diagnosis, prognosis, therapeutic monitoring or any combination of these applications; (2) a labeled binding partner to the antibody; (3) a solid phase (such as a reagent strip) upon which the anti-Hpa2 antibody is immobilized; and (4) a label or insert indicating regulatory approval for diagnostic, prognostic or therapeutic use or any combination thereof. If no labeled binding partner to the antibody is provided, the anti-Hpa2 antibody itself can be labeled with a detectable marker, e.g., a chemiluminescent, enzymatic, fluorescent, or radioactive moiety.

The invention also provides a kit comprising a nucleic acid probe capable of hybridizing to RNA encoding an Hpa2. In a specific embodiment, a kit comprises in one or more containers a pair of primers (e.g., each in the size range of 6-30 nucleotides, more preferably 10-30 nucleotides and still more preferably 10-20 nucleotides) that under appropriate reaction conditions can prime amplification of at least a portion of a nucleic acid encoding an Hpa2, such as by polymerase chain reaction (see, e.g., Innis et al., 1990, PCR Protocols, Academic Press, Inc., San Diego, Calif.), ligase chain reaction (see EP 320,308) use of Qβ replicase, cyclic probe reaction, or other methods known in the art.

Kits are also provided which allow for the detection of a plurality of Hpa2 or Hpa2-related proteins or a plurality of nucleic acids each encoding Hpa2 or an Hpa2-related protein. A kit can optionally further comprise a predetermined amount of an isolated Hpa2 or a nucleic acid encoding an Hpa2, e.g., for use as a standard or control.

A further aspect of the invention pertains to isolated or recombinant nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the tern "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

In a further aspect, the present invention provides a nucleic acid molecule comprising or consisting of a sequence which is:
  a DNA sequence shown at residues 601 or 631 to 2376 of FIG. 1 (Seq. ID No 1), residues 601 or 631 to 2202 of FIG. 2 (Seq. ID No 3), or residues 601 or 631 to 2040 of FIG. 3 (Seq. ID No 5) or its RNA equivalent, including or excluding all or part of the sequence which is 5' and/or 3' thereto;
  a sequence which is complementary to any of the sequences of (i);
  a sequence which codes for the same protein or polypeptide, as those sequences of (i) or (ii);
  a sequence which shows substantial identity with any of those of (i), (ii) and (iii); or
  a sequence which codes for a derivative or fragment of a nucleic acid molecule shown in FIG. 1, 2 or 3 (Seq. ID No 1, 3, or 5).

Nucleic acid molecules of the invention include those consisting of or comprising 1) a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of Hpa2 or a Hpa2-related protein; or 2) a nucleotide sequence of at least 10 nucleotides (more preferably, at least 15 nucleotides, at least 20 nucleotides, at least 25 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, or at least 150 nucleotides) that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence, or a portion thereof, encoding Hpa2 or a Hpa2-related protein; 3) a DNA sequence as shown at residues 601 or 631 to 2376 of FIG. 1 (Seq. ID No 1), residues 601 or 631 to 2202 of FIG. 2 (Seq. ID No 3), or residues 601 or 631 to 2040 of FIG. 3 (Seq. ID No 5) or its RNA equivalent, including or excluding all or part of the sequence which is 5' and/or 3' thereto; 4) a sequence which is complementary to any of the preceding sequences; 5) a sequence encoding the same protein or polypeptide, as the preceding sequences; 6) a sequence which shows substantial identity with any of the preceding sequences; 7) a sequence encoding a derivative or fragment of a nucleic acid molecule shown in FIG. 1, 2 or 3 (Seq. ID No 1, 3, or 5), or; 8) a sequence encoding Hpa2 or a Hpa2-related protein.

In preferred embodiments, the isolated nucleic acids of the invention consist of or comprise the nucleic acid sequences depicted in FIG. 1, 2 or 3 (Seq. ID No 1, 3, or 5). In another preferred embodiment, the isolated nucleic acids of the invention comprise at least 18, at least 20, at least 25, at least 30, or at least 40 consecutive nucleic acids of the nucleic acid sequence depicted in FIG. 1 (Seq. ID No 1).

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0. 1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome. Preferably, the isolated nucleotides of the present invention are not within a gel (i.e., a polyacrylamide separating gel) or other matrix. Specific embodiments for the cloning of a gene encoding Hpa2 or an Hpa2-related polypeptide, are presented below by way of example and not of limitation.

The nucleotide sequences of the present invention, including DNA and RNA, and comprising a sequence encoding Hpa2 or an Hpa2-related polypeptide, may be synthesized using methods known in the art, such as using conventional chemical approaches or polymerase chain reaction (PCR) amplification. The nucleotide sequences of the present invention also permit the identification and cloning of the gene encoding Hpa2 or an Hpa2-related polypeptide, for example, by screening cDNA libraries, genomic libraries or expression libraries.

Oligonucleotides encoding Hpa2 or an Hpa2-related polypeptides may be labelled and hybridized to filters containing cDNA and genomic DNA libraries. Oligonucleotides to different peptides from the same protein will often identify the same members of the library. The cDNA and genomic DNA libraries may be obtained from any suitable or desired *mammalian* species, for example from humans.

Nucleotide sequences comprising a nucleotide sequence encoding Hpa2 or an Hpa2-related polypeptide are useful for their ability to hybridize selectively with complementary stretches of genes encoding other Hpa2-related proteins. Depending on the application, a variety of hybridization conditions may be employed to obtain nucleotide sequences at least 30%, 35%, 40%, 45%, 50%, 55%, 60%, 65%, 70%, 75%, 80%, 85%, 90%, 95% or 99% identical, or 100% identical, to the sequence of a nucleotide encoding Hpa2 or an Hpa2-related polypeptide. The similarity of a given sequence to Hpa2 or an Hpa2-related polypeptide may be determined over its entire length, or over any fragment thereof. Preferably, the sequence or fragment thereof is at least 10 nucleotides (more preferably, at least 15 nucleotides, at least 20 nucleotides, at least 25 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, or at least 150 nucleotides).

For a high degree of selectivity, relatively stringent conditions are used to form the duplexes, such as low salt or high temperature conditions. As used herein, "highly stringent conditions" means hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3; incorporated herein by reference in its entirety.) For some applications, less stringent conditions for duplex formation are required. As used herein "moderately stringent conditions" means washing in 0.2×SSC/0.1% SDS at 42° C. (Ausubel et al., 1989, supra). Hybridization conditions can also be rendered more stringent by the addition of increasing amounts of formamide, to destabilize the hybrid duplex. Thus, particular hybridization conditions can be readily manipulated, and will generally be chosen depending on the desired results. In general, convenient hybridization temperatures in the presence of 50% formamide are: 42° C. for a probe which is 95 to 100% identical to the fragment of a gene encoding Hpa2 or an Hpa2-related protein, 37° C. for 90 to 95% identity and 32° C. for 70 to 90% to 90% identity.

In a preferred embodiment, the hybridization conditions are as follows: Probe—Full length Hpa2 cDNA radiolabeled by random priming. Preferably, the nucleic acid to which the probe will be hybridized is RNA. Hybridize at 68° C. for 1 hour in ExpressHyb Hybridization Solution (Clontech Laboratories, Inc., 1999). This step may also be carried out at 64, 65, 66, 67° C. for 0.5, 1.5 or 2 hours. Wash (×2) for 40 mins at 20° C. with wash 1 (2×SSC, 0.05% SDS).

This step may also be carried out at 19, 18, 17, 16° C. or room temperature, for 20, 30, 45, 60, or 190 minutes with 2.5×SSC or 3×SSC and 0.04%, 0.03% or 0.02% SDS. Wash (×2) for 40 mins at 50° C. with wash 2 (0.1×SSC, 0.1% SDS). This step may also be carried out at 40, 42, 45 or 47° C., for 20, 30, 45, 60, or 190 minutes with 0.15×SSC or 0.2×SSC and 0.03%, 0.05% or 0.07% SDS.

In the preparation of genomic libraries, DNA fragments are generated, some of which will encode parts or the whole of Hpa2 or an Hpa2-related protein. Any suitable method for preparing DNA fragments may be used in the present invention. For example, the DNA may be cleaved at specific sites using various restriction enzymes. Alternatively, one may use DNAse in the presence of manganese to fragment the DNA, or the DNA can be physically sheared, as for example, by sonication. The DNA fragments can then be separated according to size by standard techniques, including but not limited to agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, and yeast artificial chromosome (YAC). (See, e.g., Sambrook et al., 1989, *Molecular Cloning*, A Laboratory Manual, 2d Ed., Cold Spring Harbor Laboratory Press, Cold Spring Harbor, N.Y.;

Glover, D. M. (ed.), 1985, *DNA Cloning: A Practical Approach*, MRL Press, Ltd., Oxford, U.K. Vol. I, II; Ausubel F. M. et al., eds., 1989, Current Protocols in Molecular Biology, Vol. I, Green Publishing Associates, Inc., and John Wiley & sons, Inc., New York). The genomic library may be screened by nucleic acid hybridization to labeled probe (Benton and Davis, 1977, *Science* 196:180; Grunstein and Hogness, 1975, *Proc. Natl. Acad. Sci. U.S.A.* 72:3961).

Based on the present description, the genomic libraries may be screened with labelled degenerate oligonucleotide probes corresponding to the amino acid sequence of any peptide of Hpa2 or an Hpa2-related protein using optimal approaches well known in the art. Any probe used is at least 10 nucleotides, at least 15 nucleotides, at least 20 nucleotides, at least 25 nucleotides, at least 30 nucleotides, at least 40 nucleotides, at least 50 nucleotides, at least 60 nucleotides, at least 70 nucleotides, at least 80 nucleotides, or at least 100 nucleotides. Preferably a probe is 10 nucleotides or longer, and more preferably 15 nucleotides or longer.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) *Science* 261:1411-1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorgaizic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973-88). PNA monomers are then coupled in a stepwise manner to produce a chimeric molecule with a 5' PNA segment and a 3' DNA segment (Finn et al. (1996) *Nucleic Acids Res.* 24(17):3357-63). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide may include other appended groups such as peptides (e.g., for targeting host cell receptors in vivo ), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide may be conjugated to another molecule, e.g., a peptide, hybridization triggered cross-linking agent, transport agent, hybridization-triggered cleavage agent, etc.

In one embodiment, there is provided a nucleic acid molecule comprising or consisting of a sequence shown at residues 727 to 2376 of FIG. 1 (Seq. ID No 1), residues 727 to 2202 of FIG. 2 (Seq. ID No 3), or residues 727 to 2040 of FIG. 3 (Seq. ID No 5).

The term identity can also be used to describe the similarity between two individual DNA sequences. The 'bestfit' program (Smith and Waterman, Advances in applied Mathematics, 482-489 (1981)) is one example of a type of computer software used to find the best segment of similarity between two nucleic acid sequences, whilst the GAP program enables sequences to be aligned along their whole length and finds the optimal alignment by inserting spaces in either sequence as appropriate. It is preferred if sequences which show substantial identity with any of those of (i), (ii) and (iii) have e.g. at least 50%, at least 75% or at least 90% or 95% sequence identity.

The polypeptides of the present invention can be coded for by a large variety of nucleic acid molecules, taking into account the well known degeneracy of the genetic code. All of these molecules are within the scope of the present invention. They can be inserted into vectors and cloned to provide large amounts of DNA or RNA for further study. Suitable vectors may be introduced into host cells to enable the expression of polypeptides of the present invention using techniques known to the person skilled in the art.

The term 'RNA equivalent' when used above indicates that a given RNA molecule has a sequence which is complementary to that of a given DNA molecule, allowing for the fact that in RNA 'U' replaces 'T' in the genetic code. The nucleic acid molecule may be in isolated, recombinant or chemically synthetic form.

Techniques for cloning, expressing and purifying proteins and polypeptides are well known to the skilled person. DNA constructs can readily be generated using methods well known in the art. These techniques are disclosed, for example in J. Sambrook et al, *Molecular Cloning* 2$^{nd}$ *Edition*, Cold Spring Harbour Laboratory Press (1989); in Old & Primrose [*Principles of Gene Manipulation* 5th Edition, Blackwell Scientific Publications (1994); and in Stryer [*Biochemistry* 4th Edition, W H Freeman and Company (1995)]. Modifications of DNA constructs and the proteins expressed such as the addition of promoters, enhancers, signal sequences, leader sequences, translation start and stop signals and DNA stability controlling regions, or the addition of fusion partners may then be facilitated. Normally the DNA construct will be inserted into a vector which may be of phage or plasmid origin. Expression of the protein is achieved by the transformation or transfection of the vector into a host cell which may be of eukaryotic or prokaryotic origin. Such vectors and suitable host cells form yet further aspects of the present invention. Knowledge of the nucleic acid structure can be used to raise antibodies and for gene therapy. Techniques for this are well-known by those skilled in the art. By using appropriate expression systems, polypeptides of the present invention may be expressed in glycosylated or non-glycosylated form. Non-glycosylated forms can be produced by expression in prokaryotic hosts, such as *E. coli*. Polypeptides comprising N-terminal methionine may be produced using certain expression systems, whilst in others the mature polypeptide will lack this residue.

Preferred techniques for cloning, expressing and purifying a substance of the present invention are summarised below: Polypeptides may be prepared natively or under denaturing conditions and then subsequently refolded. Baculoviral expression vectors include secretory plasmids (such as pACGP67 from Pharmingen), which may have an epitope tag sequence cloned in frame (e.g. myc, V5 or His) to aid detection and allow for subsequent purification of the protein. Mammalian expression vectors may include pCDNA3 and pSecTag (both Invitrogen), and pREP9 and pCEP4 (invitrogen). *E. coli* systems include the pBad series (His tagged—Invitrogen) or pGex series (Pharamacia). In addition to nucleic acid molecules coding for polypeptides according to the present invention, referred to herein as "coding" nucleic acid molecules, the present invention also includes nucleic acid molecules complementary thereto. Thus, for example, both strands of a double stranded nucleic acid molecule are included within the scope of the present invention (whether or not they are associated with one another). Also included are mRNA molecules and complementary DNA Molecules (e.g. cDNA molecules). Nucleic acid molecules which can hybridise to any of the nucleic acid molecules discussed above are also covered by the present invention. Such nucleic acid molecules are referred to herein as "hybridising" nucleic acid molecules. Hybridising nucleic acid molecules can be useful as probes or primers, for example. Desirably such hybridising molecules are at least 10 nucleotides in length and preferably are at least 25 or at least 50 nucleotides in length. The hybridising nucleic acid molecules preferably hybridise to nucleic acids within the scope of (i), (ii), (iii), (iv) or (v) above specifically. Desirably the hybridising molecules will hybridise to such molecules under stringent hybridisation conditions. One example of stringent hybridisation conditions is where attempted hybridisation is carried out at a temperature of from about 35° C. to about 65° C. using a salt solution which is about 0.9 molar. However, the skilled person will be able to vary such conditions as appropriate in order to take into account variables such as probe length, base composition, type of ions present, etc.

Manipulation of the DNA encoding the protein is a particularly powerful technique for both modifying proteins and for generating large quantities of protein for purification purposes. This may involve the use of PCR techniques to amplify a desired nucleic acid sequence. Thus the sequence data provided herein can be used to design primers for use in PCR so that a desired sequence can be targeted and then amplified to a high degree.

Typically primers will be at least five nucleotides long and will generally be at least ten nucleotides long (e.g. fifteen to twenty-five nucleotides long). In some cases, primers of at least thirty or at least thirty-five nucleotides in length may be used. As a further alternative chemical synthesis may be used. This may be automated. Relatively short sequences may be chemically synthesised and ligated together to provide a longer sequence.

The invention provides the following nucleic acid molecules (individually and in the indicated pairs) which may be used as primers or probes:

| Sequence | Name | Seq. ID |
|---|---|---|
| GTAGACAGAGCTGCAGGTTTG | (Hepa4F1) | (Seq. ID No 12) |
| CATGATGGCTGGCTCGATTTC | (Hepa4R1) | (Seq. ID No 13) |
| TTGATGTGAGCACCAAGAACC | (Hepa4F2) | (Seq. ID No 14) |
| CAGTTCCAGAACCTGAGGAA | (Hepa4R2) | (Seq. ID No 15) |
| GCAGTTACCTGGCAACATTG | (Hepa2F1) | (Seq. ID No 16) |
| GTGACCACCTCAGCTGGAGGC | (Hepa2R1) | (Seq. ID No 17) |
| GCAGTTACCTGGCAACATTG | (Hepa2F1) | (Seq. ID No 18) |
| CTATCCGATTCCTATGCTGC | (Hepa2R2) | (Seq. ID No 19) |
| TCAAGCTGGCTGGGACTCTCAG | (Hepa3F1) | (Seq. ID No 20) |
| GATGGTGGACGACGGGAC | (Hepa3R1) | (Seq. ID No 21) |

In addition to being used as primers and/or probes, hybridising nucleic acid molecules of the present invention can be used as anti-sense molecules to alter the expression of substances of the present invention by binding to complementary nucleic acid molecules. This technique can be used in anti-sense therapy.

A hybridising nucleic acid molecule of the present invention may have a high degree of sequence identity along its length with a nucleic acid molecule within the scope of (i)-(v) above (e.g. at least 50%, at least 75% or at least 90% or 95% sequence identity). As will be appreciated by the skilled person, the higher the sequence identity a given single stranded nucleic acid molecule has with another nucleic acid molecule, the greater the likelihood that it will hybridise to a nucleic acid molecule which is complementary to that other nucleic acid molecule under appropriate conditions.

In view of the foregoing description the skilled person will appreciate that a large number of nucleic acids are within the scope of the present invention. Unless the context indicates otherwise, nucleic acid molecules of the present invention may have one or more of the following characteristics:

they may be DNA or RNA;

they may be single or double stranded;

they may be provided in recombinant form i.e. covalently linked to a 5' and/or a 3' flanking sequence to provide a molecule which does not occur in nature;

they may be provided without 5' and/or 3' flanking sequences which normally occur in nature;

they may be provided in substantially pure form. Thus they may be provided in a form which is substantially free from contaminating proteins and/or from other nucleic acids;

they may be provided with introns or without introns (e.g. as cDNA).

The inventors have also found a mouse homologue of the human protein. Thus, according to further aspect of the present invention, there is provided a polypeptide which:

(a) comprises the amino acid sequence shown in FIG. 8 (Seq. ID No 8);

(b) is a derivative having one or more amino acid substitutions, deletions or insertions relative to a substance as defined in a), above; or (c) is a fragment of a substance as defined in a) above, which is at least five or ten amino acids long (d) is an analog, fusion protein, ortholog, homolog, fragment, derivative, isoform or variant of the sequences of a), b) or c) or fragment of any of the preceding.

In a further aspect, the present invention provides a nucleic acid molecule comprising or consisting of a sequence which is:
- a DNA sequence shown in FIG. 8b (Seq. ID No 7) or its RNA equivalent;
- a sequence which is complementary to any of the sequences of (i);
- a sequence which codes for the same protein or polypeptide, as those sequences of (i) or (ii);
- a sequence which shows substantial identity with any of those of (i), (ii) and (iii); or
- a sequence which codes for any of the polypeptides described in a), b), c) or d) above, including a derivative or fragment of a nucleic acid molecule shown in FIG. 8b (Seq. ID No 7).

The nucleotide sequence coding for Hpa2 or an Hpa2-related peptide, can be inserted into an appropriate expression vector, i.e., a vector which contains the necessary elements for the transcription and translation of the inserted protein-coding sequence. The necessary transcriptional and translational signals can also be supplied by the native gene encoding the Hpa2 or its flanking regions, or the native gene encoding the Hpa2-related polypeptide or its flanking regions. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, a nucleotide sequence encoding a human gene (or a nucleotide sequence encoding a functionally active portion of a human Hpa2) is expressed. In yet another embodiment, a fragment of an Hpa2 comprising a domain of the Hpa2 is expressed.

Any of the methods previously described for the insertion of DNA fragments into a vector may be used to construct expression vectors containing a chimeric gene consisting of appropriate transcriptional and translational control signals and the protein coding sequences. These methods may include in vitro recombinant DNA and synthetic techniques and in vivo recombinants (genetic recombination). Expression of nucleic acid sequence encoding Hpa2 or fragment thereof may be regulated by a second nucleic acid sequence so that the Hpa2 or fragment is expressed in a host transformed with the recombinant DNA molecule. For example, expression of an Hpa2 may be controlled by any promoter or enhancer element known in the art. Promoters which may be used to control the expression of the gene encoding Hpa2 or an Hpa2-related polypeptide include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the b-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5):619-631; Morelli et al., 1999, Gen. Virol. 80:571-83) and gonadotropic releasing hormone gene control region which is active in the hypothalamus (Mason et al., 1986, Science 234:1372-1378).

In a specific embodiment, a vector is used that comprises a promoter operably linked to an Hpa2-encoding nucleic acid, one or more origins of replication, and, optionally, one or more selectable markers (e.g., an antibiotic resistance gene).

In a specific embodiment, an expression construct is made by subcloning Hpa2 or an Hpa2-related polypeptide coding sequence into the EcoRI restriction site of each of the three pGEX vectors (Glutathione S-Transferase expression vectors; Smith and Johnson, 1988, Gene 7:31-40). This allows for the expression of the Hpa2 product or Hpa2-related polypeptide from the subclone in the correct reading frame.

In mammalian host cells, a number of viral-based expression systems may be utilized. In cases where an adenovirus is used as an expression vector, the Hpa2 coding sequence or Hpa2-related polypeptide coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

Expression vectors containing inserts of a gene encoding Hpa2 or an Hpa2-related polypeptide can be identified by three general approaches: (a) nucleic acid hybridization, (b) presence or absence of "marker" gene functions, and (c) expression of inserted sequences. In the first approach, the presence of a gene encoding an Hpa2 inserted in an expression vector can be detected by nucleic acid hybridization using probes comprising sequences that are homologous to an inserted gene encoding an Hpa2. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a gene encoding an Hpa2 in the vector. For example, if the gene encoding the Hpa2 is inserted within the marker gene sequence of the vector, recombinants containing the gene encoding the Hpa2 insert can be identified by the absence of the marker gene function. In the third approach, recombinant expression vectors can be identified by assaying the gene product (i.e., Hpa2) expressed by the recombinant. Such assays can be based, for example, on the physical or functional properties of the Hpa2 in in vitro assay systems, e.g., binding with anti-Hpa2 antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Hpa2 or Hpa2-related polypeptide may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321N1 human astrocytoma (Proc. Natl Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is preferred. For example, cell lines which stably express the differentially expressed or pathway gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-GarHpa2n, et al., 1981, J. Mol. Biol. 150:1); and hygro, which confers resistance to hygromycin (Santerre, et al., 1984, Gene 30:147) genes.

In other specific embodiments, the Hpa2, fragment, analog, or derivative may be expressed as a fusion, or chimeric protein product (comprising the protein, fragment, analog, or derivative joined via a peptide bond to a heterologous protein sequence). For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification, increase half-life in vivo, and enhance the delivery of an antigen across an epithelial barrier to the immune system. An increase in the half-life in vivo and facilitated purification has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature,* 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT publications WO 96/22024 and WO 99/04813).

Nucleic acids encoding an Hpa2, a fragment of an Hpa2, an Hpa2-related polypeptide, or a fragment of an Hpa2-related polypeptide can fused to an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, *Proc. Natl. Acad. Sci.* USA 88:8972-897).

Fusion proteins can be made by ligating the appropriate nucleic acid sequences encoding the desired amino acid sequences to each other by methods known in the art, in the proper coding frame, and expressing the chimeric product by methods commonly known in the art. Alternatively, a fusion protein may be made by protein synthetic techniques, e.g., by use of a peptide synthesizer.

Both cDNA and genomic sequences can be cloned and expressed. Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

When used herein, "treatment/therapy" includes any regime that can benefit a human or non-human animal, and "comprising/having" covers anything consisting only of a specified feature/characteristic, as well as anything with that feature/characteristic, but which also has one or more additional features/characteristics.

Preferred features of each aspect of the invention are as for each of the other aspects mutatis mutandis. The prior art documents mentioned herein are incorporated to the fullest extent permitted by law.

EXAMPLES

The present invention will now be described in more detail in the following non-limiting examples.

Example 1

Figure 6:
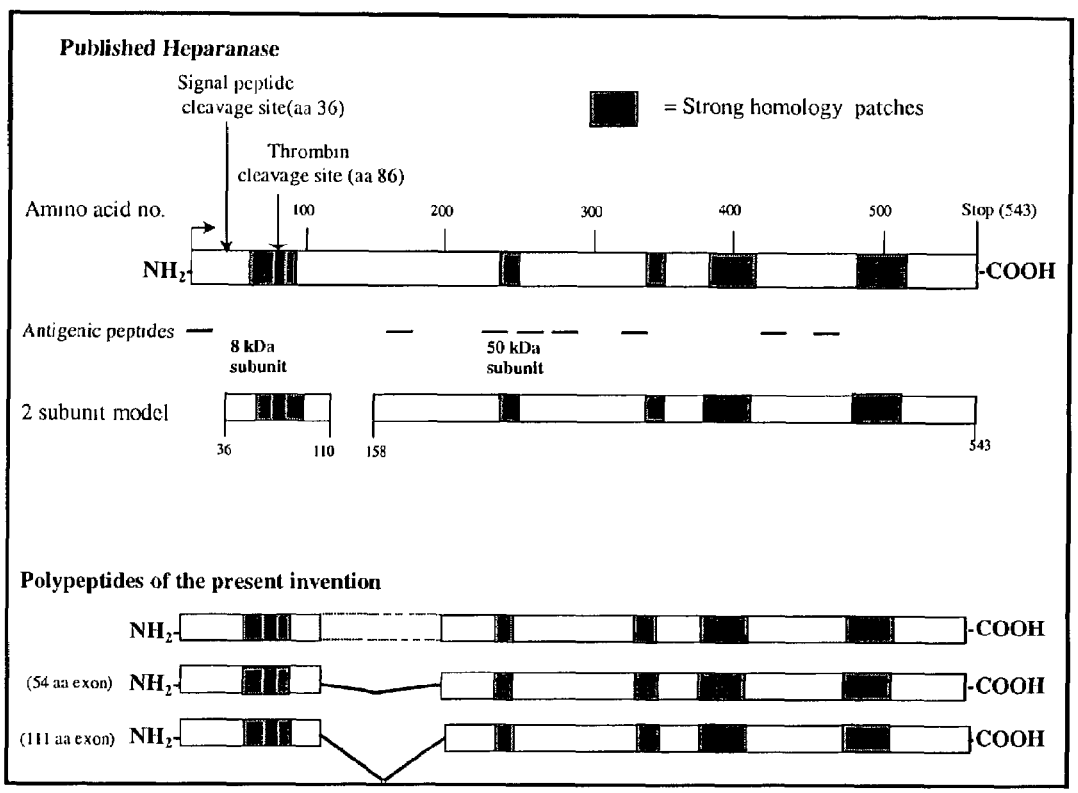
FIG. 6 illustrates the homology between the sequences (Seq. ID No 2, Seq. ID No 4, and Seq. ID No 6) of the heparanase-like proteins of the present invention and that of human heparanase.

Identification of Heparanase-Like Protein Sequences from the Incyte LifeSeq Database The published full-length amino acid sequence of human heparanase was compared to the DNA sequence databases GenBank and Incyte LifeSeq (July 1999 release). The amino acid sequence was entered into the Basic Local Alignment Search Tool programme, Gapped BLAST (Altschul et al, *Nucleic Acids Res.* 25: 3389-3402, 1997) and the programme was run with default parameters in the version TBLASTN, in which the entire database is electronically translated in six reading frames and each putative translation compared to the input sequence. No new homologous sequences were found in GenBank. Putative translated sequences of three previously unidentified sequences from LifeSeq displayed significant homology to human heparanase. The Incyte identification numbers for these sequences were: 139678.1; 273691.1; 117316.1, hereinafter referred to as EST1, EST2 and EST3, respectively. Homology was deemed significant according to the parameters set for the search programme and by our own observations of 65%, 60% and 44% overall similarity, respectively, between the published sequence and the ESTs, with blocks of 5 or more contiguous identical or similar amino acids found in each alignment. Conceptual translation followed by electronic sequence alignment showed homology to the published heparanase protein which is consistent with conservation of protein function and commonality of evolutionary origin (see FIGS. 4 and 6). Further searches based on TBLASTN comparison of regions of highest conservation revealed that no other known human gene had homology with the heparanase sequence Example 2

PCR Cloning of Heparanase-Like cDNA and Identification of Splice Variants

Forward and reverse oligonucleotide primers were designed around the sequence of all three EST sequences (see FIG. 3). Primer combinations of Hepa2F1/Hepa3R1 link up Ests 139678.1 and 273691.1. Primer combinations Hepa4F1/Hepa2R1 link up Ests 117316.1 and 139678.1.

PCR reactions were carried out using the following conditions:

5 ul of Human mammary gland marathon-ready cDNA (Clontech), 1 μl of Advantage 2 cDNA polymerase mix (Clontech) in a buffer containing 50 mM KCl, 10 mM Tris-HCl, 1.5 mM MgCl2, pH 8.3; 0.2 mM each of dATP, dCTP, dGTP, dTTP and 10 pmoles of oligonucleotide primers. Reactions were routinely made to a final volume of 50 μl and amplification carried out in a PE GeneAmp-Systems 9700 PCR machine with the following cycling conditions: initial denaturation of 94° C. for 1 minute followed by 30 cycles of 94° C. for 30 seconds, 55° C. for 30 seconds and 72° C. for 2 minutes. Reaction products were resolved by standard agarose gel electrophoresis and stained with SYBR Green (Molecular Probes, Oregon, USA).

Between Ests 117316.1 and 139678.1, at least three splice variants were visible on gels, and these bands were cut from gels, and were cloned using the TOPO II rapid cloning kit (Invitrogen, The Netherlands). Three corresponding sequences were obtained (see FIGS. 1-3, and Seq. ID No 1, 3, 5)). Each sequence has two putative start codons, one at nucleotides 601-603 (methionine 1) and the other at nucleotides 631-633 (methionine 43).

Example 3

Antibody Generation

Antigenicity mapping for the novel protein (The Binding Site, UK), gave three potential peptide sequences. These are synthesised and used to generate antibodies in sheep. Each of these peptides generates antibodies which will recognise all three splice forms of the novel protein. The three peptides, and their location within the novel protein are:

```
                                  (Seq. ID No 9)
Pep 1      137-159:   QPIRIYSRASLYGPNIGRPRKNV (Seq. ID No 10)
Pep 2      201-224:   DTLSDQIRKIQKVVNTYTPGKKIW (Seq. ID No 11)
Pep 3      304-325:   AVHVAGLQRKPRPGRVIRDKLRIYA
```

Example 4

Radiation Hybrid Mapping

Chromosomal localisation for the novel heparanase-like peptides was determined using radiation hybrid mapping, with the low resolution GENEBRIDGE 4 Radiation Hybrid Mapping Panel of 93 RH clones of the whole human genome (Research Genetics, Huntsville, Ala., USA ). This is a subset of the 199 clone panel developed by a collaboration between the laboratories of Peter Goodfellow and Jean Weissenbach. Chromosome localisation of markers was performed by accessing the server at http://www-genome.wi.mit.edu/cgi-bin/contig/rhmapper.pl. The results showed that the novel protein was localised to chromosome 10 at 10q23-24. This region is associated with several types of cancer. The published heparanase gene is found on chromosome 4.

Example 5

Expression Profile

Standard quantitative Taqman PCR techniques were used to examine the relative mRNA levels (expressed per ng DNA) for the heparanase like protein of the present invention, in a number of different tissues and cell lines. Two heparanase-like protein specific primers were used, which did not differentiate between the different splice forms. The results of this analysis show relatively high levels of heparanase like protein mRNA in several tissues including brain, breast, testes and in a pancreatic cancer cell line, whereas it is low in most others (see FIG. 7).

Example 6

Identification of Homologue in Mouse

A mouse EST sequence with homology to the human heparanase sequence was obtained by BLAST searching: IMAGE clone 1378452. These sequences are shown aligned with the hpa2 ones in FIGS. 8*a* & *b* (Seq. ID No 7 and 8). Significant homology to the human heparanase-like sequence was seen at both nucleotide and encoded amino acid levels.

SEQUENCE LISTING

<160> NUMBER OF SEQ ID NOS: 23

<210> SEQ ID NO 1
<211> LENGTH: 2636
<212> TYPE: DNA
<213> ORGANISM: Homo sapiens
<220> FEATURE:
<221> NAME/KEY: misc_feature
<222> LOCATION: (1)...(2636)
<223> OTHER INFORMATION: n = A,T,C or G

<400> SEQUENCE: 1

| | | | | | |
|---|---|---|---|---|---|
| atccagagcn | tctcagggaa | ggacgtaaaa | acgagaccct | ttgctctgta | cccagacggt | 60 |
| acaacggcat | ggtttggatt | cctccctctg | cttcctgacc | ctagagggtt | aaattaggag | 120 |
| ggtacaacgc | cacccttttc | tcctccttcc | cgcctgctcc | cctcccctta | cctttaaaaa | 180 |
| gttaaaaaat | gtctgcagta | gaaatctctt | aaaggggcgg | tgccggtgta | cgagttctct | 240 |
| tggcaagagt | cacggggaag | gctggctagg | ggcgtgagtt | cgctccacca | gcaccaaaac | 300 |

-continued

```
actgaaaaaa aaaattaaaa aaaattaaaa aaaaaaaaag aaaaaaacaa aacgagcgag    360
cgagcgagcg agagagagag agagcgggag agagagagag tgtgtgtgtg ttgggggggt    420
ggtgggagga agggaaaaaa aggggggaaa aaggcggacg agagtgtgtg tgtgttgggg    480
gggtggtggg aggaagggaa aaaaggggg gaaaaggcg acagacaca cactttagat    540 aaggacaatt agtcactagc gagacccagt aggaagagag gtttaaatca gagggattga    600
atgagggtgc tttgtgcctt ccctgaagcc atgccctcca gcaactcccg ccccccgcg    660 tgcctagccc cggggctct ctacttggct ctgttgctcc atctctccct ttcctcccag    720
gctggagaca ggagacccctt gcctgtagac agagctgcag gtttgaagga aaagaccctg    780
attctacttg atgtgagcac caagaaccca gtcaggacag tcaatgagaa cttcctctct    840
ctgcagctgg atccgtccat cattcatgat ggctggctcg atttcctaag ctccaagcgc    900
ttggtgaccc tggcccgggg actttcgccc gcctttctgc gcttcggggg caaaaggacc    960
gacttcctgc agttccagaa cctgaggaac ccggcgaaaa gccgcggggg cccgggcccg   1020
gattactatc tcaaaaacta tgaggatgac attgttcgaa gtgatgttgc cttagataaa   1080
cagaaaggct gcaagattgc ccagcaccct gatgttatgc tggagctcca agggagaag   1140 gcagctcaga tgcatctggt tcttctaaag gagcaattct ccaatactta cagtaatctc   1200
atattaacag ccaggtctct agacaaactt tataactttg ctgattgctc tggactccac   1260
ctgatatttg ctctaaatgc actgcgtcgt aatcccaata actcctggan cagttctagt   1320
gccctgagtc tgttgaagta cagcgcnagc aaaaagtaca acatttcttg ggaactgggt   1380
aatgagccaa ataactatcg gaccatgcat ggccgggcag taaatggcag ccagttggga   1440
aaggattaca tccagctgaa gagcctgttg cagcccatcc ggatttattc cagagccagc   1500
ttatatggcc ctaatattgg gcggccgagg aagaatgtca tcgccctcct agatggattc   1560
atgaaggtgg caggaagtac agtagatgca gttacctggc aacattgcta cattgatggc   1620
cgggtggtca aggtgatgga cttcctgaaa actcgcctgt tagacacact ctctgaccag   1680
attaggaaaa ttcagaaagt ggttaataca tacactccag gaaagaagat ttggcttgaa   1740
ggtgtggtga ccacctcagc tggaggcaca acaatctat ccgattccta tgctgcagga   1800
ttcttatggt tgaacacttt aggaatgctg gccaatcagg gcattgatgt cgtgatacgg   1860
cactcatttt ttgaccatgg atacaatcac ctcgtggacc agaattttaa cccattacca   1920
gactactggc tctctctcct ctacaagcgc ctgatcggcc ccaaagtctt ggctgtgcat   1980
gtggctgggc tccagcggaa gccacggcct ggccgagtga tccgggacaa actaaggatt   2040
tatgctcact gcacaaacca ccacaaccac aactacgttc gtgggtccat tacacttttt   2100
atcatcaact tgcatcgatc aagaaagaaa atcaagctgg ctgggactct cagagacaag   2160
ctggttcacc agtaccctgct gcagccctat gggcaggagg gcctaaagtc caagtcagtg   2220
caactgaatg gccagccctt agtgatggtg gacgacggga ccctcccaga attgaagccc   2280 cgccccttc gggccggccg gacattggtc atccctccag tcaccatggg cttttttgtg   2340
gtcaagaatg tcaatgcttt ggcctgccgc taccgataag ctatcctcac actcatggct   2400
accagtgggc ctgctgggct gcttccactc ctccactcca gtagtatcct ctgttttcag   2460
acatcctagc aaccagcccc tgctgcccca tcctgctgga atcaacacag acttgctctc   2520
caaagagact aaatgtcata gcgtgatctt agcctaggta ggcccacatcc atcccaaagg   2580 aaaatgtaga catcacctgt acctatataa ggataaaggc atgtgtatag agcaaa       2636
```

```
<210> SEQ ID NO 2
<211> LENGTH: 592
<212> TYPE: PRT
<213> ORGANISM: Homo sapiens
<220> FEATURE:
<221> NAME/KEY: VARIANT
<222> LOCATION: (1)...(592)
<223> OTHER INFORMATION: Xaa = Any Amino Acid

<400> SEQUENCE: 2
```

| | | | | | | | | | | | | | | | |
|---|---|---|---|---|---|---|---|---|---|---|---|---|---|---|---|
| Met | Arg | Val | Leu | Cys | Ala | Phe | Pro | Glu | Ala | Met | Pro | Ser | Ser | Asn | Ser |
| 1 | | | | 5 | | | | | 10 | | | | | 15 | |
| Arg | Pro | Pro | Ala | Cys | Leu | Ala | Pro | Gly | Ala | Leu | Tyr | Leu | Ala | Leu | Leu |
| | | | 20 | | | | | 25 | | | | | 30 | | |
| Leu | His | Leu | Ser | Leu | Ser | Ser | Gln | Ala | Gly | Asp | Arg | Arg | Pro | Leu | Pro |
| | | 35 | | | | | 40 | | | | | 45 | | | |
| Val | Asp | Arg | Ala | Ala | Gly | Leu | Lys | Glu | Lys | Thr | Leu | Ile | Leu | Leu | Asp |
| 50 | | | | | 55 | | | | | 60 | | | | | |
| Val | Ser | Thr | Lys | Asn | Pro | Val | Arg | Thr | Val | Asn | Glu | Asn | Phe | Leu | Ser |
| 65 | | | | | 70 | | | | | 75 | | | | | 80 |
| Leu | Gln | Leu | Asp | Pro | Ser | Ile | Ile | His | Asp | Gly | Trp | Leu | Asp | Phe | Leu |
| | | | | 85 | | | | | 90 | | | | | 95 | |
| Ser | Ser | Lys | Arg | Leu | Val | Thr | Leu | Ala | Arg | Gly | Leu | Ser | Pro | Ala | Phe |
| | | | 100 | | | | | 105 | | | | | 110 | | |
| Leu | Arg | Phe | Gly | Gly | Lys | Arg | Thr | Asp | Phe | Leu | Gln | Phe | Gln | Asn | Leu |
| | | 115 | | | | | 120 | | | | | 125 | | | |
| Arg | Asn | Pro | Ala | Lys | Ser | Arg | Gly | Gly | Pro | Gly | Pro | Asp | Tyr | Tyr | Leu |
| 130 | | | | | 135 | | | | | 140 | | | | | |
| Lys | Asn | Tyr | Glu | Asp | Asp | Ile | Val | Arg | Ser | Asp | Val | Ala | Leu | Asp | Lys |
| 145 | | | | | 150 | | | | | 155 | | | | | 160 |
| Gln | Lys | Gly | Cys | Lys | Ile | Ala | Gln | His | Pro | Asp | Val | Met | Leu | Glu | Leu |
| | | | | 165 | | | | | 170 | | | | | 175 | |
| Gln | Arg | Glu | Lys | Ala | Ala | Gln | Met | His | Leu | Val | Leu | Lys | Glu | Gln |
| | | | 180 | | | | | 185 | | | | | 190 | |
| Phe | Ser | Asn | Thr | Tyr | Ser | Asn | Leu | Ile | Leu | Thr | Ala | Arg | Ser | Leu | Asp |
| | | | 195 | | | | | 200 | | | | | 205 | | |
| Lys | Leu | Tyr | Asn | Phe | Ala | Asp | Cys | Ser | Gly | Leu | His | Leu | Ile | Phe | Ala |
| | 210 | | | | | 215 | | | | | 220 | | | | |
| Leu | Asn | Ala | Leu | Arg | Arg | Asn | Pro | Asn | Asn | Ser | Trp | Xaa | Ser | Ser | Ser |
| 225 | | | | | 230 | | | | | 235 | | | | | 240 |
| Ala | Leu | Ser | Leu | Leu | Lys | Tyr | Ser | Ala | Ser | Lys | Tyr | Asn | Ile | Ser |
| | | | | 245 | | | | | 250 | | | | | 255 |
| Trp | Glu | Leu | Gly | Asn | Glu | Pro | Asn | Asn | Tyr | Arg | Thr | Met | His | Gly | Arg |
| | | | 260 | | | | | 265 | | | | | 270 | | |
| Ala | Val | Asn | Gly | Ser | Gln | Leu | Gly | Lys | Asp | Tyr | Ile | Gln | Leu | Lys | Ser |
| | | | 275 | | | | | 280 | | | | | 285 | | |
| Leu | Leu | Gln | Pro | Ile | Arg | Ile | Tyr | Ser | Arg | Ala | Ser | Leu | Tyr | Gly | Pro |
| | | 290 | | | | | 295 | | | | | 300 | | | |
| Asn | Ile | Gly | Arg | Pro | Arg | Lys | Asn | Val | Ile | Ala | Leu | Leu | Asp | Gly | Phe |
| 305 | | | | | 310 | | | | | 315 | | | | | 320 |
| Met | Lys | Val | Ala | Gly | Ser | Thr | Val | Asp | Ala | Val | Thr | Trp | Gln | His | Cys |
| | | | | 325 | | | | | 330 | | | | | 335 | |
| Tyr | Ile | Asp | Gly | Arg | Val | Val | Lys | Val | Met | Asp | Phe | Leu | Lys | Thr | Arg |
| | | | 340 | | | | | 345 | | | | | 350 | | |
| Leu | Leu | Asp | Thr | Leu | Ser | Asp | Gln | Ile | Arg | Lys | Ile | Gln | Lys | Val | Val |

```
                  355                 360                 365
Asn Thr Tyr Thr Pro Gly Lys Lys Ile Trp Leu Glu Gly Val Val Thr
            370                 375                 380

Thr Ser Ala Gly Gly Thr Asn Asn Leu Ser Asp Ser Tyr Ala Ala Gly
385                 390                 395                 400

Phe Leu Trp Leu Asn Thr Leu Gly Met Leu Ala Asn Gln Gly Ile Asp
                405                 410                 415

Val Val Ile Arg His Ser Phe Phe Asp His Gly Tyr Asn His Leu Val
            420                 425                 430

Asp Gln Asn Phe Asn Pro Leu Pro Asp Tyr Trp Leu Ser Leu Leu Tyr
            435                 440                 445

Lys Arg Leu Ile Gly Pro Lys Val Leu Ala Val His Val Ala Gly Leu
450                 455                 460

Gln Arg Lys Pro Arg Pro Gly Arg Val Ile Arg Asp Lys Leu Arg Ile
465                 470                 475                 480

Tyr Ala His Cys Thr Asn His His Asn His Asn Tyr Val Arg Gly Ser
                485                 490                 495

Ile Thr Leu Phe Ile Ile Asn Leu His Arg Ser Arg Lys Lys Ile Lys
                500                 505                 510

Leu Ala Gly Thr Leu Arg Asp Lys Leu Val His Gln Tyr Leu Leu Gln
            515                 520                 525

Pro Tyr Gly Gln Glu Gly Leu Lys Ser Lys Ser Val Gln Leu Asn Gly
            530                 535                 540

Gln Pro Leu Val Met Val Asp Asp Gly Thr Leu Pro Glu Leu Lys Pro
545                 550                 555                 560

Arg Pro Leu Arg Ala Gly Arg Thr Leu Val Ile Pro Pro Val Thr Met
                565                 570                 575

Gly Phe Phe Val Val Lys Asn Val Asn Ala Leu Ala Cys Arg Tyr Arg
                580                 585                 590

<210> SEQ ID NO 3
<211> LENGTH: 2462
<212> TYPE: DNA
<213> ORGANISM: Homo sapiens
<220> FEATURE:
<221> NAME/KEY: misc_feature
<222> LOCATION: (1)...(2462)
<223> OTHER INFORMATION: n = A,T,C or G

<400> SEQUENCE: 3
atccagagcn tctcagggaa ggacgtaaaa acgagaccct ttgctctgta cccagacggt      60
acaacggcat ggtttggatt cctccctctg cttcctgacc ctagagggtt aaattaggag     120
ggtacaacgc caccctttc tcctccttcc cgcctgctcc cctcccctta cctttaaaaa     180
gttaaaaaat gtctgcagta gaaatctctt aaagggcgg tgccggtgta cgagttctct     240
tggcaagagt cacggggaag gctggctagg ggcgtgagtt cgctccacca gcaccaaaac     300
actgaaaaaa aaaattaaaa aaaattaaaa aaaaaaaaag aaaaaaacaa acgagcgag     360 cgagcgagcg agagagagag agagcggag agagagagag tgtgtgtgtg ttggggggt     420 ggtgggagga aggaaaaaa aggggggaaa aaggcggacg agagtgtgtg tgtgttgggg     480
gggtggtggg aggaagggaa aaaaggggg gaaaaggcg acagacaca cactttagat     540 aaggacaatt agtcactagc gagacccagt aggaagagag gtttaaatca gagggattga     600
atgagggtgc tttgtgcctt ccctgaagcc atgccctcca gcaactcccg ccccccgcg     660 tgcctagccc cgggggctct ctacttggct ctgttgctcc atctctccct ttcctcccag     720
```

-continued

```
gctggagaca ggagacccctt gcctgtagac agagctgcag gtttgaagga aaagaccctg    780
attctacttg atgtgagcac caagaaccca gtcaggacag tcaatgagaa cttcctctct    840
ctgcagctgg atccgtccat cattcatgat ggctggctcg atttcctaag ctccaagcgc    900
ttggtgaccc tggcccgggg actttcgccc gcctttctgc gcttcggggg caaaaggacc    960
gacttcctgc agttccagaa cctgaggaac cggcgaaaa gccgcggggg cccgggcccg   1020
gattactatc tcaaaaacta tgaggatgac attgttcgaa gtgatgttgc cttagataaa   1080
cagaaaggct gcaagattgc ccagcaccct gatgttatgc tggagctcca aagggagaag   1140
gcagctcaga tgcatctggt tcttctaaag gagcaattct ccaatactta cagtaatctc   1200
atattaacag agccaaataa ctatcggacc atgcatggcc gggcagtaaa tggcagccag   1260
ttgggaaagg attacatcca gctgaagagc ctgttgcagc ccatccggat ttattccaga   1320
gccagcttat atgggcctaa tattgggcgg ccgaggaaga atgtcatcgc cctcctagat   1380
ggattcatga aggtggcagg aagtacagta gatgcagtta cctggcaaca ttgctacatt   1440
gatggccggg tggtcaaggt gatggacttc ctgaaaactc gcctgttaga cacactctct   1500
gaccagatta ggaaaattca gaaagtggtt aatacataca ctccaggaaa aagatttgg    1560
cttgaaggtg tggtgaccac ctcagctgga ggcacaaaca atctatccga ttcctatgct   1620
gcaggattct tatggttgaa cactttagga atgctggcca atcagggcat tgatgtcgtg   1680
atacggcact cattttttga ccatggatac aatcacctcg tggaccagaa ttttaaccca   1740
ttaccagact actggctctc tctcctctac aagcgcctga tcggcccaa agtcttggct   1800
gtgcatgtgg ctgggctcca gcggaagcca cggcctggcc gagtgatccg ggacaaacta   1860
aggatttatg ctcactgcac aaaccaccac aaccacaact acgttcgtgg gtccattaca   1920
cttttttatca tcaacttgca tcgatcaaga aagaaaatca agctggctgg gactctcaga   1980
gacaagctgg ttcaccagta cctgctgcag ccctatgggc aggagggcct aaagtccaag   2040
tcagtgcaac tgaatggcca gcccttagtg atggtggacg acgggaccct cccagaattg   2100
aagccccgcc cccttcgggc cggccggaca ttggtcatcc ctccagtcac catgggcttt   2160
tttgtggtca agaatgtcaa tgctttggcc tgccgctacc gataagctat cctcacactc   2220
atggctacca gtgggcctgc tgggctgctt ccactcctcc actccagtag tatcctctgt   2280
tttcagacat cctagcaacc agcccctgct gccccatcct gctggaatca acacagactt   2340
gctctccaaa gagactaaat gtcatagcgt gatcttagcc taggtaggcc acatccatcc   2400
caaaggaaaa tgtagacatc acctgtacct atataaggat aaaggcatgt gtatagagca   2460
aa                                                                  2462
```

<210> SEQ ID NO 4
<211> LENGTH: 534
<212> TYPE: PRT
<213> ORGANISM: Homo sapiens

<400> SEQUENCE: 4

Met Arg Val Leu Cys Ala Phe Pro Glu Ala Met Pro Ser Ser Asn Ser
1               5                   10                  15

Arg Pro Pro Ala Cys Leu Ala Pro Gly Ala Leu Tyr Leu Ala Leu Leu
            20                  25                  30

Leu His Leu Ser Leu Ser Ser Gln Ala Gly Asp Arg Arg Pro Leu Pro
        35                  40                  45

Val Asp Arg Ala Ala Gly Leu Lys Glu Lys Thr Leu Ile Leu Leu Asp

```
                 50                  55                  60
Val Ser Thr Lys Asn Pro Val Arg Thr Val Asn Glu Asn Phe Leu Ser
 65                  70                  75                  80

Leu Gln Leu Asp Pro Ser Ile Ile His Asp Gly Trp Leu Asp Phe Leu
                 85                  90                  95

Ser Ser Lys Arg Leu Val Thr Leu Ala Arg Gly Leu Ser Pro Ala Phe
                100                 105                 110

Leu Arg Phe Gly Gly Lys Arg Thr Asp Phe Leu Gln Phe Gln Asn Leu
                115                 120                 125

Arg Asn Pro Ala Lys Ser Arg Gly Gly Pro Gly Pro Asp Tyr Tyr Leu
                130                 135                 140

Lys Asn Tyr Glu Asp Asp Ile Val Arg Ser Asp Val Ala Leu Asp Lys
145                 150                 155                 160

Gln Lys Gly Cys Lys Ile Ala Gln His Pro Asp Val Met Leu Glu Leu
                165                 170                 175

Gln Arg Glu Lys Ala Ala Gln Met His Leu Val Leu Leu Lys Glu Gln
                180                 185                 190

Phe Ser Asn Thr Tyr Ser Asn Leu Ile Leu Thr Glu Pro Asn Asn Tyr
                195                 200                 205

Arg Thr Met His Gly Arg Ala Val Asn Gly Ser Gln Leu Gly Lys Asp
                210                 215                 220

Tyr Ile Gln Leu Lys Ser Leu Leu Gln Pro Ile Arg Ile Tyr Ser Arg
225                 230                 235                 240

Ala Ser Leu Tyr Gly Pro Asn Ile Gly Arg Pro Arg Lys Asn Val Ile
                245                 250                 255

Ala Leu Leu Asp Gly Phe Met Lys Val Ala Gly Ser Thr Val Asp Ala
                260                 265                 270

Val Thr Trp Gln His Cys Tyr Ile Asp Gly Arg Val Val Lys Val Met
                275                 280                 285

Asp Phe Leu Lys Thr Arg Leu Leu Asp Thr Leu Ser Asp Gln Ile Arg
                290                 295                 300

Lys Ile Gln Lys Val Val Asn Thr Tyr Thr Pro Gly Lys Lys Ile Trp
305                 310                 315                 320

Leu Glu Gly Val Val Thr Thr Ser Ala Gly Gly Thr Asn Asn Leu Ser
                325                 330                 335

Asp Ser Tyr Ala Ala Gly Phe Leu Trp Leu Asn Thr Leu Gly Met Leu
                340                 345                 350

Ala Asn Gln Gly Ile Asp Val Val Ile Arg His Ser Phe Phe Asp His
                355                 360                 365

Gly Tyr Asn His Leu Val Asp Gln Asn Phe Asn Pro Leu Pro Asp Tyr
                370                 375                 380

Trp Leu Ser Leu Leu Tyr Lys Arg Leu Ile Gly Pro Lys Val Leu Ala
385                 390                 395                 400

Val His Val Ala Gly Leu Gln Arg Lys Pro Arg Pro Gly Arg Val Ile
                405                 410                 415

Arg Asp Lys Leu Arg Ile Tyr Ala His Cys Thr Asn His His Asn His
                420                 425                 430

Asn Tyr Val Arg Gly Ser Ile Thr Leu Phe Ile Ile Asn Leu His Arg
                435                 440                 445

Ser Arg Lys Lys Ile Lys Leu Ala Gly Thr Leu Arg Asp Lys Leu Val
                450                 455                 460

His Gln Tyr Leu Leu Gln Pro Tyr Gly Gln Glu Gly Leu Lys Ser Lys
465                 470                 475                 480
```

Ser Val Gln Leu Asn Gly Gln Pro Leu Val Met Val Asp Asp Gly Thr
                485                 490                 495

Leu Pro Glu Leu Lys Pro Arg Pro Leu Arg Ala Gly Arg Thr Leu Val
            500                 505                 510

Ile Pro Pro Val Thr Met Gly Phe Phe Val Lys Asn Val Asn Ala
        515                 520                 525

Leu Ala Cys Arg Tyr Arg
    530

<210> SEQ ID NO 5
<211> LENGTH: 2300
<212> TYPE: DNA
<213> ORGANISM: Homo sapiens
<220> FEATURE:
<221> NAME/KEY: misc_feature
<222> LOCATION: (1)...(2300)
<223> OTHER INFORMATION: n = A,T,C or G

<400> SEQUENCE: 5

| | | | | |
|---|---|---|---|---|
| atccagagcn | tctcagggaa | ggacgtaaaa | acgagaccct | ttgctctgta | cccagacggt | 60 |
| acaacggcat | ggtttggatt | cctccctctg | cttcctgacc | ctagagggtt | aaattaggag | 120 |
| ggtacaacgc | cacccttttc | tcctccttcc | cgcctgctcc | cctcccctta | cctttaaaaa | 180 |
| gttaaaaaat | gtctgcagta | gaaatctctt | aaagggggcgg | tgccggtgta | cgagttctct | 240 |
| tggcaagagt | cacggggaag | gctggctagg | ggcgtgagtt | cgctccacca | gcaccaaaac | 300 |
| actgaaaaaa | aaaattaaaa | aaaattaaaa | aaaaaaaaag | aaaaaaacaa | aacgagcgag | 360 |
| cgagcgagcg | agagagagag | agagcgggag | agagagagag | tgtgtgtgtg | ttgggggggt | 420 |
| ggtgggagga | agggaaaaaa | aggggggaaa | aaggcggacg | agagtgtgtg | tgtgttgggg | 480 |
| gggtggtggg | aggaagggaa | aaaaggggg | gaaaaggcg | gacagacaca | cactttagat | 540 |
| aaggacaatt | agtcactagc | gagacccagt | aggaagagag | gtttaaatca | gagggattga | 600 |
| atgagggtgc | tttgtgcctt | ccctgaagcc | atgccctcca | gcaactcccg | ccccccgcg | 660 |
| tgcctagccc | cgggggctct | ctacttggct | ctgttgctcc | atctctcccct | ttcctcccag | 720 |
| gctggagaca | ggagacccct | gcctgtagac | agagctgcag | gtttgaagga | aaagaccctg | 780 |
| attctacttg | atgtgagcac | caagaaccca | gtcaggacag | tcaatgagaa | cttcctctct | 840 |
| ctgcagctgg | atccgtccat | cattcatgat | ggctggctcg | atttcctaag | ctccaagcgc | 900 |
| ttggtgaccc | tggcccgggg | actttcgccc | gcctttctgc | gcttcggggg | caaaaggacc | 960 |
| gacttcctgc | agttccagaa | cctgaggaac | ccggcgaaaa | gccgcggggg | cccgggcccg | 1020 |
| gattactatc | tcaaaaacta | tgaggatgag | ccaaataact | atcggaccat | gcatggccgg | 1080 |
| gcagtaaatg | gcagccagtt | gggaaaggat | tacatccagc | tgaagagcct | gttgcagccc | 1140 |
| atccggattt | attccagagc | cagcttatat | ggccctaata | ttgggcggcc | gaggaagaat | 1200 |
| gtcatcgccc | tcctagatgg | attcatgaag | gtggcaggaa | gtacagtaga | tgcagttacc | 1260 |
| tggcaacatt | gctacattga | tggccgggtg | gtcaaggtga | tggacttcct | gaaaactcgc | 1320 |
| ctgttagaca | cactctctga | ccagattagg | aaaattcaga | aagtggttaa | tacatacact | 1380 |
| ccaggaaaga | agatttggct | tgaaggtgtg | gtgaccacct | cagctggagg | cacaaacaat | 1440 |
| ctatccgatt | cctatgctgc | aggattctta | tggttgaaca | ctttaggaat | gctggccaat | 1500 |
| cagggcattg | atgtcgtgat | acggcactca | ttttttgacc | atggatacaa | tcacctcgtg | 1560 |
| gaccagaatt | ttaacccatt | accagactac | tggctctctc | tcctctacaa | gcgcctgatc | 1620 |

-continued

```
ggccccaaag tcttggctgt gcatgtggct gggctccagc ggaagccacg gcctggccga      1680
gtgatccggg acaaactaag gatttatgct cactgcacaa accaccacaa ccacaactac      1740
gttcgtgggt ccattacact ttttatcatc aacttgcatc gatcaagaaa gaaaatcaag      1800
ctggctggga ctctcagaga caagctggtt caccagtacc tgctgcagcc ctatgggcag      1860
gagggcctaa agtccaagtc agtgcaactg aatggccagc ccttagtgat ggtggacgac      1920
gggaccctcc cagaattgaa gccccgcccc cttcgggccg gccggacatt ggtcatccct      1980
ccagtcacca tgggcttttt tgtggtcaag aatgtcaatg ctttggcctg ccgctaccga      2040
taagctatcc tcacactcat ggctaccagt gggcctgctg ggctgcttcc actcctccac      2100
tccagtagta tcctctgttt tcagacatcc tagcaaccag ccctgctgc cccatcctgc       2160 tggaatcaac acagacttgc tctccaaaga gactaaatgt catagcgtga tcttagccta      2220
ggtaggccac atccatccca aaggaaaatg tagacatcac ctgtacctat ataaggataa      2280
aggcatgtgt atagagcaaa                                                  2300
```

```
<210> SEQ ID NO 6
<211> LENGTH: 480
<212> TYPE: PRT
<213> ORGANISM: Homo sapiens

<400> SEQUENCE: 6
```

```
Met Arg Val Leu Cys Ala Phe Pro Glu Ala Met Pro Ser Ser Asn Ser
  1               5                  10                  15

Arg Pro Pro Ala Cys Leu Ala Pro Gly Ala Leu Tyr Leu Ala Leu Leu
             20                  25                  30

Leu His Leu Ser Leu Ser Ser Gln Ala Gly Asp Arg Arg Pro Leu Pro
         35                  40                  45

Val Asp Arg Ala Ala Gly Leu Lys Glu Lys Thr Leu Ile Leu Leu Asp
     50                  55                  60

Val Ser Thr Lys Asn Pro Val Arg Thr Val Asn Glu Asn Phe Leu Ser
 65                  70                  75                  80

Leu Gln Leu Asp Pro Ser Ile Ile His Asp Gly Trp Leu Asp Phe Leu
                 85                  90                  95

Ser Ser Lys Arg Leu Val Thr Leu Ala Arg Gly Leu Ser Pro Ala Phe
            100                 105                 110

Leu Arg Phe Gly Gly Lys Arg Thr Asp Phe Leu Gln Phe Gln Asn Leu
        115                 120                 125

Arg Asn Pro Ala Lys Ser Arg Gly Gly Pro Gly Pro Asp Tyr Tyr Leu
    130                 135                 140

Lys Asn Tyr Glu Asp Glu Pro Asn Asn Tyr Arg Thr Met His Gly Arg
145                 150                 155                 160

Ala Val Asn Gly Ser Gln Leu Gly Lys Asp Tyr Ile Gln Leu Lys Ser
                165                 170                 175

Leu Leu Gln Pro Ile Arg Ile Tyr Ser Arg Ala Ser Leu Tyr Gly Pro
            180                 185                 190

Asn Ile Gly Arg Pro Arg Lys Asn Val Ile Ala Leu Leu Asp Gly Phe
        195                 200                 205

Met Lys Val Ala Gly Ser Thr Val Asp Ala Val Thr Trp Gln His Cys
    210                 215                 220

Tyr Ile Asp Gly Arg Val Val Lys Val Met Asp Phe Leu Lys Thr Arg
225                 230                 235                 240

Leu Leu Asp Thr Leu Ser Asp Gln Ile Arg Lys Ile Gln Lys Val Val
                245                 250                 255
```

```
Asn Thr Tyr Thr Pro Gly Lys Lys Ile Trp Leu Glu Gly Val Val Thr
            260                 265                 270
Thr Ser Ala Gly Gly Thr Asn Asn Leu Ser Asp Ser Tyr Ala Ala Gly
        275                 280                 285
Phe Leu Trp Leu Asn Thr Leu Gly Met Leu Ala Asn Gln Gly Ile Asp
    290                 295                 300
Val Val Ile Arg His Ser Phe Asp His Gly Tyr Asn His Leu Val
305                 310                 315                 320
Asp Gln Asn Phe Asn Pro Leu Pro Asp Tyr Trp Leu Ser Leu Leu Tyr
                325                 330                 335
Lys Arg Leu Ile Gly Pro Lys Val Leu Ala Val His Val Ala Gly Leu
            340                 345                 350
Gln Arg Lys Pro Arg Pro Gly Arg Val Ile Arg Asp Lys Leu Arg Ile
        355                 360                 365
Tyr Ala His Cys Thr Asn His His Asn His Asn Tyr Val Arg Gly Ser
    370                 375                 380
Ile Thr Leu Phe Ile Ile Asn Leu His Arg Ser Arg Lys Lys Ile Lys
385                 390                 395                 400
Leu Ala Gly Thr Leu Arg Asp Lys Leu Val His Gln Tyr Leu Leu Gln
                405                 410                 415
Pro Tyr Gly Gln Glu Gly Leu Lys Ser Lys Ser Val Gln Leu Asn Gly
            420                 425                 430
Gln Pro Leu Val Met Val Asp Asp Gly Thr Leu Pro Glu Leu Lys Pro
        435                 440                 445
Arg Pro Leu Arg Ala Gly Arg Thr Leu Val Ile Pro Pro Val Thr Met
    450                 455                 460
Gly Phe Phe Val Val Lys Asn Val Asn Ala Leu Ala Cys Arg Tyr Arg
465                 470                 475                 480

<210> SEQ ID NO 7
<211> LENGTH: 330
<212> TYPE: DNA
<213> ORGANISM: Mus musculus

<400> SEQUENCE: 7
gacattgtcc ggagtgatgt tgccttggac aagcagaaag gctgtaagat tgcccagcac    60
cctgatgtca tgctggagct ccagagagag aaggcatcca gactgtctgg ttcttctgaa   120
ggagcaatac tccaatactt acagtaacct catattaaca ggtctctaga caaactttat   180
aactttgctg attgctctgg actccacctg atatttgctc taaatgcact gcgtcgtaat   240
cccaataact cctggaacag ttctagtgcc ctgagcctgt tgaagtacag tgccagcaaa   300
aagtacaaca tttcttggga actgggtaat                                    330

<210> SEQ ID NO 8
<211> LENGTH: 115
<212> TYPE: PRT
<213> ORGANISM: Homo sapiens

<400> SEQUENCE: 8

Phe Gly Arg Gly Ser Cys Leu Met Tyr Arg Asp Ile Val Arg Ser Asp
1               5                  10                  15
Val Ala Leu Asp Lys Gln Lys Gly Cys Lys Ile Gly Gln His Pro Asp
            20                  25                  30
Val Met Leu Glu Leu Gln Arg Glu Lys Ala Ser Arg Leu Ser Gly Ser
        35                  40                  45
```

```
Ser Glu Gly Ala Ile Leu Gln Tyr Leu Gln Pro His Ile Asn Arg Ser
        50                  55                  60

Leu Asp Lys Leu Tyr Asn Phe Ala Asp Cys Ser Gly Leu His Leu Ile
65                  70                  75                  80

Phe Ala Leu Asn Ala Leu Arg Arg Asn Pro Asn Asn Ser Trp Asn Ser
                85                  90                  95

Ser Ser Ala Leu Ser Leu Leu Lys Tyr Ser Ala Ser Lys Lys Tyr Asn
                100                 105                 110

Ile Ser Trp
        115

<210> SEQ ID NO 9
<211> LENGTH: 23
<212> TYPE: PRT
<213> ORGANISM: Homo sapiens

<400> SEQUENCE: 9

Gln Pro Ile Arg Ile Tyr Ser Arg Ala Ser Leu Tyr Gly Pro Asn Ile
1               5                   10                  15

Gly Arg Pro Arg Lys Asn Val
            20

<210> SEQ ID NO 10
<211> LENGTH: 24
<212> TYPE: PRT
<213> ORGANISM: Homo sapiens

<400> SEQUENCE: 10

Asp Thr Leu Ser Asp Gln Ile Arg Lys Ile Gln Lys Val Val Asn Thr
1               5                   10                  15

Tyr Thr Pro Gly Lys Lys Ile Trp
            20

<210> SEQ ID NO 11
<211> LENGTH: 25
<212> TYPE: PRT
<213> ORGANISM: Homo sapiens

<400> SEQUENCE: 11

Ala Val His Val Ala Gly Leu Gln Arg Lys Pro Arg Pro Gly Arg Val
1               5                   10                  15

Ile Arg Asp Lys Leu Arg Ile Tyr Ala
            20                  25

<210> SEQ ID NO 12
<211> LENGTH: 21
<212> TYPE: DNA
<213> ORGANISM: Homo sapiens

<400> SEQUENCE: 12
gtagacagag ctgcaggttt g                                        21

<210> SEQ ID NO 13
<211> LENGTH: 21
<212> TYPE: DNA
<213> ORGANISM: Homo sapiens

<400> SEQUENCE: 13
catgatggct ggctcgattt c                                        21
```

```
<210> SEQ ID NO 14
<211> LENGTH: 21
<212> TYPE: DNA
<213> ORGANISM: Homo sapiens

<400> SEQUENCE: 14
ttgatgtgag caccaagaac c                                              21

<210> SEQ ID NO 15
<211> LENGTH: 20
<212> TYPE: DNA
<213> ORGANISM: Homo sapiens

<400> SEQUENCE: 15
cagttccaga acctgaggaa                                                20

<210> SEQ ID NO 16
<211> LENGTH: 20
<212> TYPE: DNA
<213> ORGANISM: Homo sapiens

<400> SEQUENCE: 16
gcagttacct ggcaacattg                                                20

<210> SEQ ID NO 17
<211> LENGTH: 21
<212> TYPE: DNA
<213> ORGANISM: Homo sapiens

<400> SEQUENCE: 17
gtgaccacct cagctggagg c                                              21

<210> SEQ ID NO 18
<211> LENGTH: 20
<212> TYPE: DNA
<213> ORGANISM: Homo sapiens

<400> SEQUENCE: 18
gcagttacct ggcaacattg                                                20

<210> SEQ ID NO 19
<211> LENGTH: 20
<212> TYPE: DNA
<213> ORGANISM: Homo sapiens

<400> SEQUENCE: 19
ctatccgatt cctatgctgc                                                20

<210> SEQ ID NO 20
<211> LENGTH: 22
<212> TYPE: DNA
<213> ORGANISM: Homo sapiens

<400> SEQUENCE: 20
tcaagctggc tgggactctc ag                                             22

<210> SEQ ID NO 21
<211> LENGTH: 18
<212> TYPE: DNA
<213> ORGANISM: Homo sapiens

<400> SEQUENCE: 21
gatggtggac gacgggac                                                  18
```

```
<210> SEQ ID NO 22
<211> LENGTH: 400
<212> TYPE: DNA
<213> ORGANISM: Homo sapiens
<220> FEATURE:
<221> NAME/KEY: misc_feature
<222> LOCATION: (1)...(400)
<223> OTHER INFORMATION: n = A,T,C or G

<400> SEQUENCE: 22
tatctcaaaa actatgagga tgacattgtt cgaagtgatg ttgccttaga taaacagaaa      60
ggctgcaaga ttgcccagca ccctgatgtt atgctggagc tccaaaggga gaaggcagct     120
cagatgcatc tggttctttt aaaggagcaa ttctccaata cttacagtaa tctcatatta     180
acagccaggt ctctagacaa actttataac tttgctgatt gctctggact ccacctgata     240
tttgctctaa atgcactgcg tcgtaatccc aataactcct ggancagttc tagtgccctg     300
agtctgttga agtacagcgc nagcaaaaag tacaacattt cttgggaact gggtaataac     360
tatcggacca tgcatggccg ggcagtaaat ggcagccagt                           400

<210> SEQ ID NO 23
<211> LENGTH: 166
<212> TYPE: PRT
<213> ORGANISM: Homo sapiens
<220> FEATURE:
<221> NAME/KEY: VARIANT
<222> LOCATION: (1)...(166)
<223> OTHER INFORMATION: Xaa = Any Amino Acid

<400> SEQUENCE: 23

Thr Leu Ala Arg Gly Leu Ser Pro Ala Phe Leu Arg Phe Gly Gly Lys
 1               5                  10                  15

Arg Thr Asp Phe Leu Gln Phe Gln Asn Leu Arg Asn Pro Ala Lys Ser
            20                  25                  30

Arg Gly Gly Pro Gly Pro Asp Tyr Tyr Leu Lys Asn Tyr Glu Asp Asp
        35                  40                  45

Ile Val Arg Ser Asp Val Ala Leu Asp Lys Gln Lys Gly Cys Lys Ile
    50                  55                  60

Ala Gln His Pro Asp Val Met Leu Glu Leu Gln Arg Glu Lys Ala Ala
65                  70                  75                  80

Gln Met His Leu Val Leu Leu Lys Glu Gln Phe Ser Asn Thr Tyr Ser
                85                  90                  95

Asn Leu Ile Leu Thr Ala Arg Ser Leu Asp Lys Leu Tyr Asn Phe Ala
            100                 105                 110

Asp Cys Ser Gly Leu His Leu Ile Phe Ala Leu Asn Ala Leu Arg Arg
        115                 120                 125

Asn Pro Asn Asn Ser Trp Xaa Ser Ser Ser Ala Leu Ser Leu Leu Lys
    130                 135                 140

Tyr Ser Ala Ser Lys Lys Tyr Asn Ile Ser Trp Glu Leu Gly Glu Pro
145                 150                 155                 160

Asn Asn Tyr Arg Thr Met
                165
```

The invention claimed is:

1. A polypeptide having heparanase activity which consists of the amino acid sequence of SEQ ID NO: 4, starting at residue 1, 2, 11, 12 or 43.

2. A pharmaceutical composition comprising a polypeptide according to claim 1 and a pharmaceutically acceptable carrier.

3. A kit comprising a composition according to claim 2, optionally including instruction for the use of said composition.

* * * * *